US010571396B2

(12) United States Patent
Schramm et al.

(10) Patent No.: US 10,571,396 B2
(45) Date of Patent: Feb. 25, 2020

(54) METHODS AND SYSTEMS FOR FLUORESCENCE DETECTION

(71) Applicant: Molecular Devices, LLC, Sunnyvale, CA (US)

(72) Inventors: Annegret Schramm, Piding (DE); Michael Katzlinger, Eugendorf (AT)

(73) Assignee: Molecular Devices, LLC, San Jose, CA (US)

( * ) Notice: Subject to any disclaimer, the term of this patent is extended or adjusted under 35 U.S.C. 154(b) by 754 days.

(21) Appl. No.: 15/053,428

(22) Filed: Feb. 25, 2016

(65) Prior Publication Data

US 2016/0299079 A1 Oct. 13, 2016

Related U.S. Application Data

(63) Continuation-in-part of application No. 14/682,026, filed on Apr. 8, 2015.

(51) Int. Cl.
*G01N 21/64* (2006.01)

(52) U.S. Cl.
CPC ..... *G01N 21/6428* (2013.01); *G01N 21/6408* (2013.01); *G01N 2021/6441* (2013.01)

(58) Field of Classification Search
None
See application file for complete search history.

(56) References Cited

U.S. PATENT DOCUMENTS

| 4,591,550 | A  | * | 5/1986  | Hafeman  | G01N 27/327 204/403.08 |
|---|---|---|---|---|---|
| 5,674,698 | A  | * | 10/1997 | Zarling  | B82Y 15/00 422/504 |
| 6,268,222 | B1 | * | 7/2001  | Chandler | G01N 33/54346 435/174 |
| 6,537,829 | B1 |   | 3/2003  | Zarling et al. | |
| 9,188,527 | B2 | * | 11/2015 | Atzler   | G01N 21/645 |
| 2003/0228703 | A1 | * | 12/2003 | Hoppe | G01N 21/6428 436/172 |
| 2004/0265938 | A1 | * | 12/2004 | Remacle  | C12Q 1/42 435/7.92 |
| 2009/0142856 | A1 |   | 6/2009  | Hudack et al. | |
| 2010/0035349 | A1 |   | 2/2010  | Bau et al. | |
| 2010/0184046 | A1 | * | 7/2010  | Klass | C12Q 1/6886 435/7.1 |
| 2012/0283575 | A1 | * | 11/2012 | Rao | A61B 5/015 600/476 |
| 2013/0150265 | A1 |   | 6/2013  | Balog et al. | |

FOREIGN PATENT DOCUMENTS

WO 2013184168 A1 12/2013

OTHER PUBLICATIONS

Kuningas et al., Simultaneous Use of Time-Resolved Fluoresence and Anti-Stokes Photoluminescence in a Bioaffinty Assay, Anal. Chem., 77, (2005), p. 2826-2834 (Year: 2005).*
Geddes, Chris D. Review in Fluorescence 2009. New York: Springer, (2011). Print. (5 pages) (Year: 2011).*
International Search Report and Written Opinion for PCT/US2016/019563 dated Jun. 30, 2016.
Riuttamaki, T, Upconverting Phosphor Technology: Exceptional Photoluminescent Properties Light Up Homogeneous Bioanalytical Assays, Turun Yliopiston Julkaisuja, Annales Universitatis Turkuensis, Turku 2011.
Sigma Aldrich, Sunstone® Luminescent UCP Nanocrystals, article from Sigma Aldrich's Website at http://www.sigmaaldrich.com/technical-documents/articles/biology/upconverting-ucp-nanocrystals.html#applications.

* cited by examiner

*Primary Examiner* — Christine Foster
*Assistant Examiner* — Ellen J Marcsisin
(74) *Attorney, Agent, or Firm* — Olive Law Group

(57) ABSTRACT

The present invention is directed to multiplexed fluorescence detection, including time-resolved fluorescence (TRF) detection. A combination of spectral and temporal differences in fluorescence emission and spectral differences in excitation is used to enhance the ability to separate signals in an assay from multiple fluorescent labels. Different classes of labels may be utilized, including upconversion phosphors as well as lanthanide chelates and transition metal chelates. The methods may be implemented in optical plate readers, including cartridge-based multi-mode readers.

23 Claims, 20 Drawing Sheets

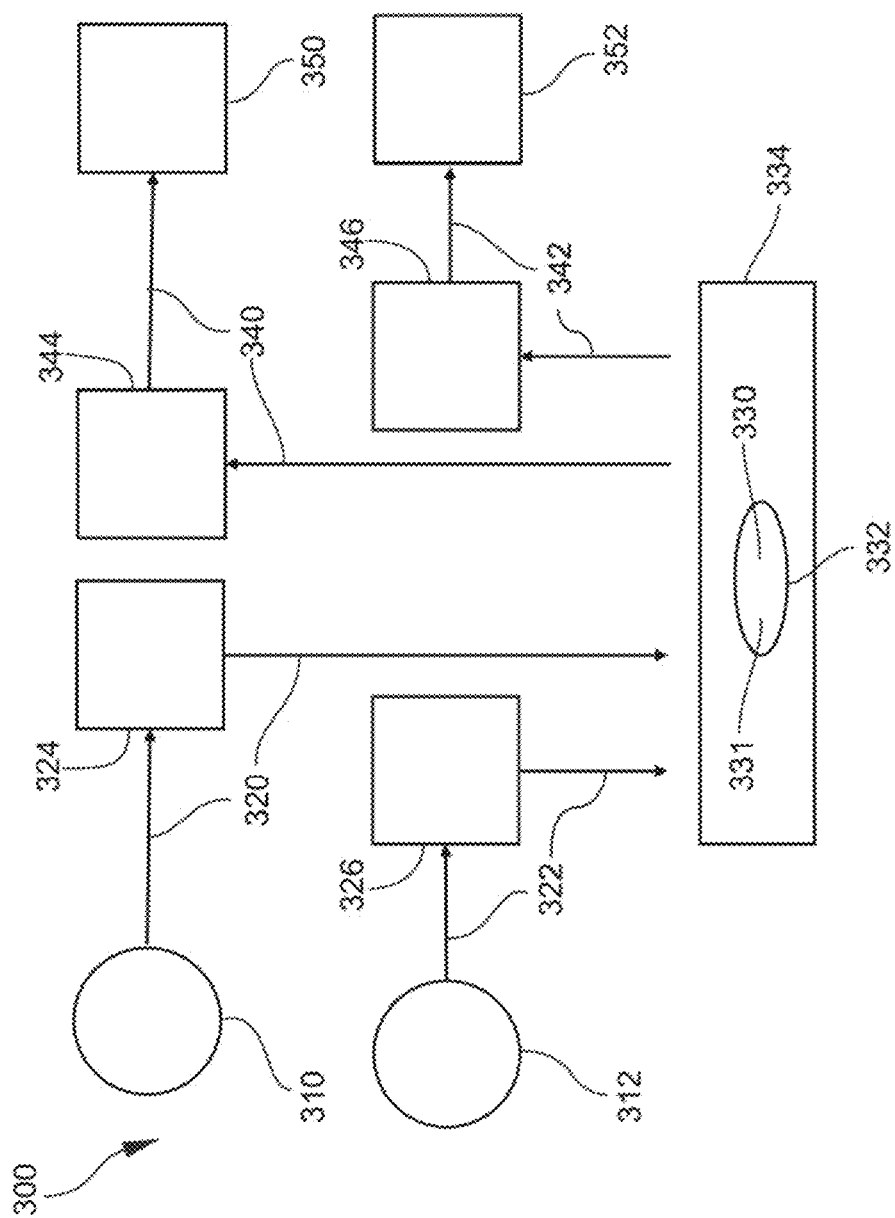

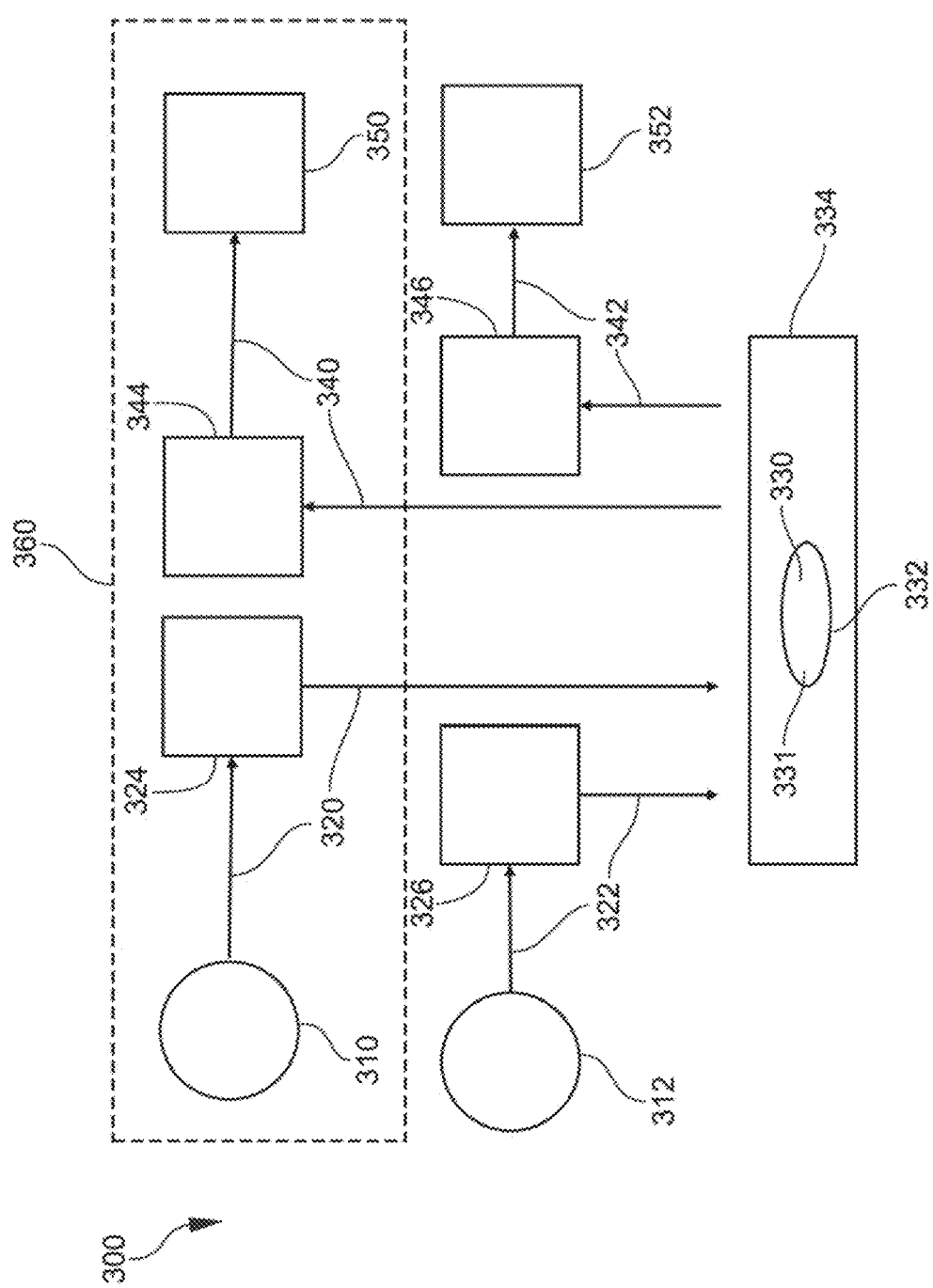

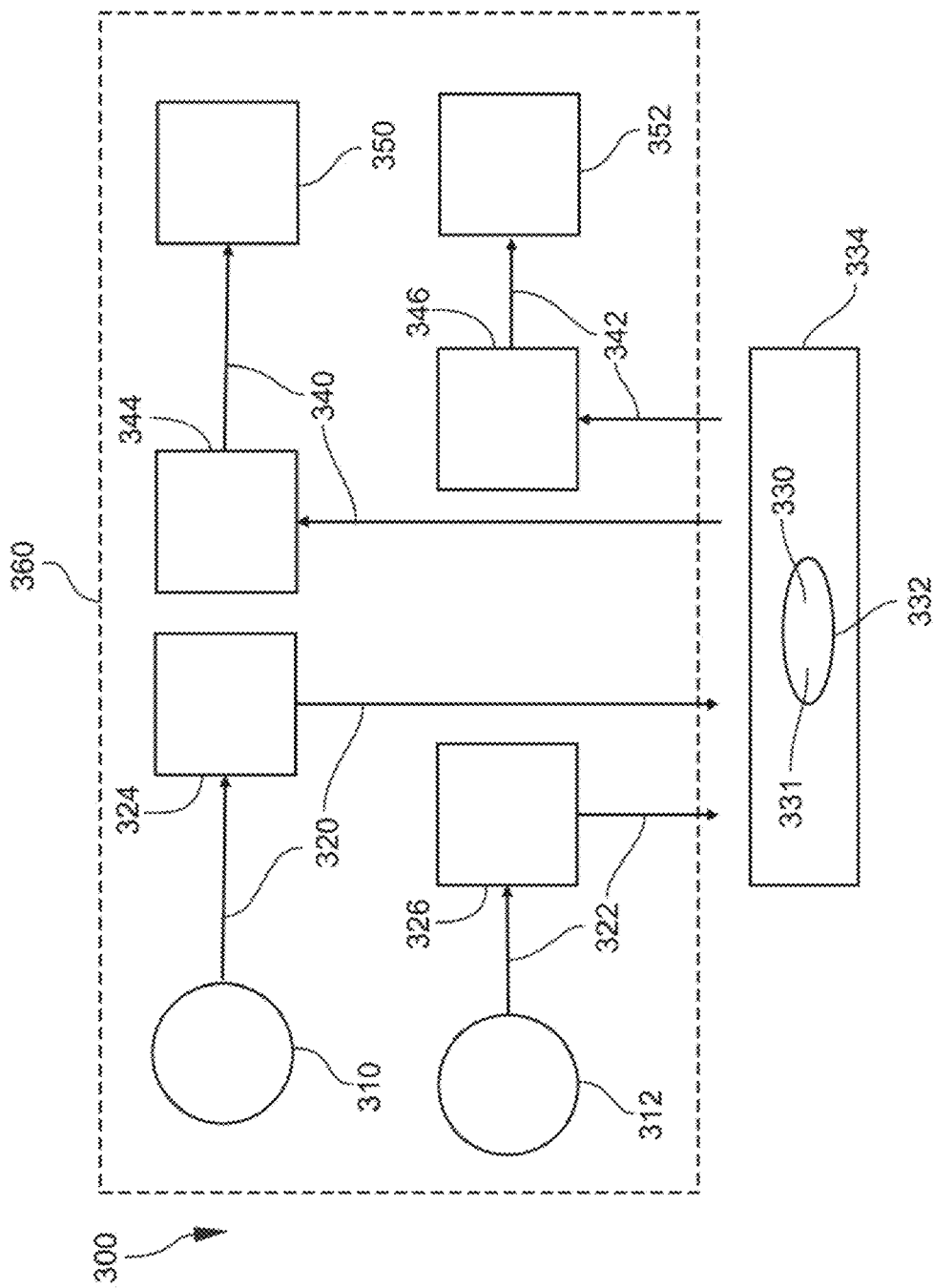

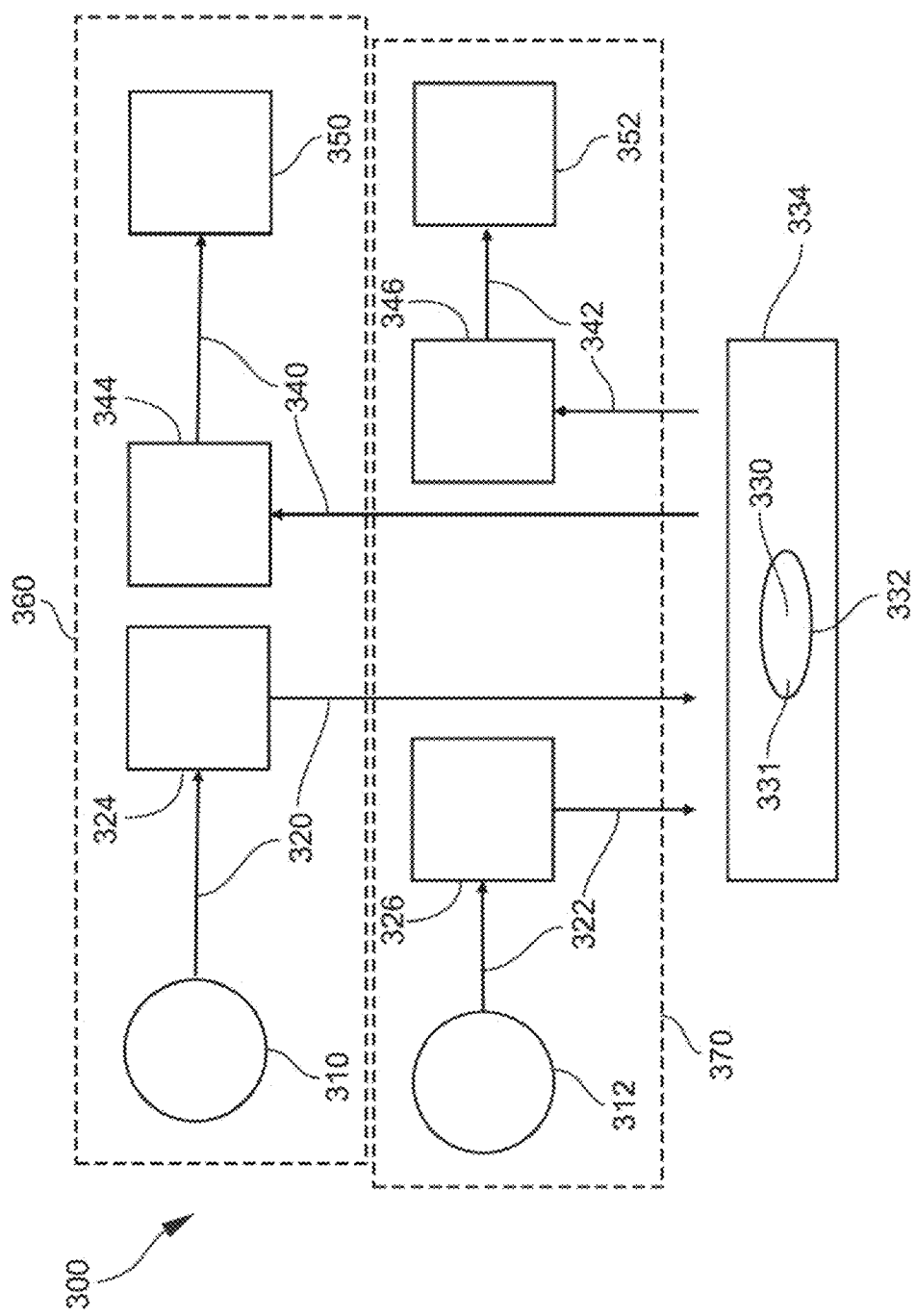

METHODS AND SYSTEMS FOR FLUORESCENCE DETECTION

RELATED APPLICATIONS

This is a Continuation-In-Part application of U.S. patent application Ser. No. 14/682,026 filed Apr. 8, 2015, titled "METHOD AND SYSTEM FOR MULTIPLEXED TIME-RESOLVED FLUORESCENCE DETECTION," the content of which is incorporated by reference herein in its entirety.

TECHNICAL FIELD

The present invention generally relates to methods, apparatuses, and systems for fluorescence-based detection or measurement of samples, particularly multiplexed detection utilizing different fluorophores. The invention may implement different types of techniques for fluorescence-based detection, including normal fluorescence detection (FD) and time-resolved fluorescence (TRF) detection.

BACKGROUND

Protein detection and characterization is an important task for pharmaceutical and clinical research. Chemiluminescence (CL) is a common method for detection of proteins in biochemical analyses or on surface-bound and spatially separated proteins. An example of the latter is the method of sodium dodecyl sulfate-polyacrylamide gel electrophoresis (SDS-PAGE) with electrophoretic transfer of proteins to a membrane, referred to as Western Blot (WB) analysis (Towbin et al. (1979) Proc. Natl. Acad. Sci. U.S.A. 76(9):4350-4354; Renart et al. (1979) Proc. Natl. Acad. Sci. U.S.A. 76(7):3116-3120). Electro-chemiluminescence (ECL) has also been applied to detect proteins bound to spots in specially designed multiwell plates (e.g., MULTI SPOT® and MULTI-ARRAY™ plates and SECTOR™ instruments, Meso Scale Discovery, a division of Meso Scale Diagnostics, LLC, Gaithersburg, Md.).

An advantage of CL and ECL is very high sensitivity with limits of detection for proteins in solution in the sub-picogram/ml range. However, these systems produce transient signals, are not chemically stable, and require a complicated procedure to produce the chemical reaction required for detection. They are also non-linear systems (i.e., one probe produces many photons) and have poor reproducibility so are not suitable for applications where quantitation of protein amount is desired. A last, but significant limitation is the inability to multiplex multiple CL signals. Their emissions are very broad and that makes the ability to detect two different CL emissions from the same spatial location very challenging.

Fluorescence (FL) probes overcome some of the limitations of CL. They provide ability for better quantitation since the relationship between excitation photons and emission photons is, in general, linear. They are also more versatile as there is no need to provide access to the probes by other reactive molecules. In general, FL probes are also more stable, especially when protected from light as they are generally non-reactive chemical species. Perhaps the most important advantage of FL probes is that they provide the ability to perform multiplexing. FL molecules come in a wide variety of forms with a wide range of excitation and emission bands. Thus two (or more) probes at the same spatial location can be independently excited and detected with minimal overlap (or cross-talk) between detection channels. The ability to detect up to four independent fluorophores from the same spatial location is regularly reported using color bandpass filters. Higher levels of multiplexing have been reported with flow cytometry and multispectral imaging (Stack et al. (2014) Methods 70(1):46-58; Perfetto et al. (2004) 4(8):648-655).

Unfortunately, FL probes have not demonstrated the same level of sensitivity as CL and typically have a lower dynamic range. A reason for lower sensitivity with FL probes is the presence of background from autofluorescence of co-localized material or interference of fluorescence from other probes. A different technique was developed to reduce background from autofluorescence using longer lifetime fluorescent probes called time-resolved fluorescence (TRF) (Zuchner et al. (2009) Anal. Chem. 81(22): 9449-9453; Kemper et al. (2001) Electrophoresis. 22(5):881-889; Lim et al. (1997) Anal Biochem. 245(2):184-195; Huhtinen et al. (2005) Anal. Chem. 77(8):2643-2648; Vereb et al. (1998) Biophys J. 74(5):2210-2222). In brief, autofluorescence typically has a relatively short lifetime (<20 ns) so that TRF detection is delayed in time until after the autofluorescence signal has died away. This is technically time gated detection, but has commonly been called time-resolved (Lakowicz, "Principles of Fluorescence Spectroscopy," 3rd Edition, Springer-Verlag, New York, 2006). The benefits of TRF detection have been well documented and include higher sensitivity, lower background, and wider dynamic range (Eliseeva & Bunzli (2010) Chem. Soc. Rev. 39(1):189-227; Bunzli & Piguet (2005) Chem. Soc. Rev. 34(12):1048-1077; Diamandis (1991) Clin. Chem. 37(9):1486-1491).

Multiplexing of TRF has been reported with some success. The use of Eu and Tb based probes has been demonstrated in biochemical assays using Time-Resolved Fluorescence Resonance Energy Transfer (TR-FRET) to detect two different proteins (Degorce et al. (2009) Curr. Chem. Genomics. 3:22-32; Bookout et al. (2000) J. Agric. Food Chem. 48(12):5868-5873; Hamy et al. (2001) J Biomol. Screen. 6(3):179-187). In addition, there have also been reports of multiplexing with Eu and Sm, and Eu, Tb, and Sm (Bador et al. (1987) Clin. Chem. 33(1):48-51; Heinonen et al. (1997) Clin. Chem. 43(7):1142-1150). However, these systems suffer from cross-talk as emission from one of the lanthanides bleeds into the detection channels of the other lanthanides. This limits the utility of these methods to having only one truly sensitive channel, while the other is limited by background signal from the second species.

Therefore, there is a need for an improved multiplexed system that maintains the high sensitivity, background rejection, stability, resistance to photo bleaching, and dynamic range of time-resolved fluorescence detection with minimal or no cross-talk between channels.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to an embodiment, a method for multiplexed time-resolved fluorescence (TRF) detection includes: providing a sample comprising a first fluorescent label bound to a first analyte and a second fluorescent label bound to a second analyte, wherein the first fluorescent label has a first fluorescence emission lifetime which is at least 3 times longer than background fluorescence emission lifetimes, a first excitation wavelength, and a first emission wavelength, and the second fluorescent label has a second fluorescence emission lifetime, a second excitation wavelength, and a second emission wavelength; exciting the first fluorescent label with a first excitation light having the first excitation wavelength, wherein the first fluorescent label emits a first detection signal having the first emission wavelength; exciting the second fluorescent label with a second excitation light having the second excitation wavelength, wherein the second fluorescent label emits a second detection signal having the second emission wavelength; measuring intensity of the first detection signal, wherein the intensity of the first detection signal is positively correlated with the amount of the first analyte in the sample; and measuring intensity of the second detection signal, wherein the intensity of the second detection signal is positively correlated with the amount of the second analyte in the sample; wherein the second fluorescence emission lifetime is at least 5 times longer than the first fluorescence emission lifetime.

According to another embodiment, the sample further comprises at least one additional fluorescent label bound to an additional analyte, wherein the additional fluorescent label has a label-specific excitation wavelength, a label-specific emission wavelength, and a label-specific fluorescence emission lifetime which is at least 3 times longer than background emission lifetimes; wherein the first fluorescence emission lifetime, the second fluorescence emission lifetime, and the label-specific fluorescence emission lifetime are each at least an order of magnitude different from one another. The additional fluorescent label is excited with a label-specific excitation light having the label-specific excitation wavelength, wherein the additional fluorescent label emits a label-specific detection signal having the label-specific emission wavelength. The intensity of the label-specific detection signal is then measured, wherein the intensity of the label-specific detection signal is positively correlated with the amount of the additional analyte in the sample. The at least one additional fluorescent label bound to an additional analyte may also comprise a plurality of different fluorescent labels bound to different analytes.

According to another embodiment, a multiplexed time-resolved fluorescence (TRF) detection apparatus or system is configured for performing all or part of any of the methods disclosed herein, such as the exciting and measuring steps of the method.

According to another embodiment, an apparatus or system for performing fluorescence detection includes: a processor and a memory configured for performing all or part of any of the methods disclosed herein.

According to another embodiment, a computer-readable storage medium includes instructions for performing all or part of any of the methods disclosed herein.

According to another embodiment, an apparatus or system includes the computer-readable storage medium.

According to another embodiment, a multiplexed time-resolved fluorescence (TRF) detection apparatus includes: a sample support configured for supporting a sample, the sample comprising a first fluorescent label and a second fluorescent label, wherein the first fluorescent label has a first fluorescence emission lifetime which is at least 3 times longer than background fluorescence emission lifetimes, a first excitation wavelength, and a first emission wavelength, and the second fluorescent label has a second fluorescence emission lifetime, a second excitation wavelength, and a second emission wavelength, and wherein the second fluorescence emission lifetime is at least 5 times longer than the first fluorescence emission lifetime; a light source configured for generating a first excitation light at the first excitation wavelength and a second excitation light at the second excitation wavelength; a light detector configured for measuring a first detection signal emitted from the sample in response to excitation by the first excitation light and a second detection signal emitted from the sample in response to excitation by the second excitation light; a computing device configured for: controlling the light source to generate the first excitation light and the second excitation light according to a timing sequence; and receiving an electrical output from the light detector corresponding to measurements of the first detection signal and the second detection signal.

According to another embodiment, a method for multiplexed fluorescence detection includes: providing a sample comprising a first fluorescent label bound to a first analyte and a second fluorescent label bound to a second analyte, wherein the first fluorescent label comprises an upconverting phosphor (UCP) and the second fluorescent label comprises a non-UCP label; irradiating the first fluorescent label with a first excitation light at a first excitation wavelength, wherein the first fluorescent label emits a first detection signal at a first emission wavelength; irradiating the second fluorescent label with a second excitation light at a second excitation wavelength different from the first excitation wavelength, wherein the second fluorescent label emits a second detection signal at a second emission wavelength different from the first emission wavelength; measuring an intensity of the first detection signal at a first measurement time, wherein the intensity of the first detection signal is correlated with the amount of the first analyte in the sample; ceasing irradiating the second fluorescent label; and after ceasing irradiating the second fluorescent label, measuring an intensity of the second detection signal at a second measurement time different from the first measurement time, wherein the intensity of the second detection signal is correlated with the amount of the second analyte in the sample.

According to another embodiment, the sample comprises a third fluorescent label bound to a third analyte, the third fluorescent label comprises a non-UCP label different from the second fluorescent label, and the method further includes: irradiating the third fluorescent label with a third excitation light at a third excitation wavelength different from the first excitation wavelength and the second excitation wavelength, wherein the third fluorescent label emits a third detection signal at a third emission wavelength different from the first emission wavelength and the second emission wavelength; ceasing irradiating the third fluorescent label; and after ceasing irradiating the third fluorescent label, measuring an intensity of the third detection signal at a third measurement time different from the first measurement time and the second measurement time.

According to another embodiment, a fluorescence detection apparatus is configured for performing at least the irradiating and measuring steps of any of the methods disclosed herein, and includes: a light source configured for generating the first excitation light and the second excitation light; and a light detector configured for measuring the first detection signal and the second detection signal.

According to another embodiment, a fluorescence detection apparatus includes: a sample support configured for supporting a sample, the sample comprising a first fluorescent label bound to a first analyte and a second fluorescent label bound to a second analyte, wherein the first fluorescent label comprises an upconverting phosphor (UCP) and the second fluorescent label comprises a non-UCP label; a light source configured for generating a first excitation light at a first excitation wavelength and a second excitation light at a second excitation wavelength different from the first excitation wavelength; a light detector configured for measuring a first detection signal emitted from the sample at a first emission wavelength in response to excitation by the first excitation light, and a second detection signal emitted from the sample at a second emission wavelength in response to excitation by the second excitation light; and a computing device configured for: controlling the light source to respectively generate the first excitation light and the second excitation light at predetermined excitation times and for predetermined durations; and controlling the light detector to measure the first detection signal at a first measurement time, and to measure the second detection signal at a second measurement time.

According to another embodiment, the sample comprises a third fluorescent label bound to a third analyte, the third fluorescent label comprising a non-UCP label different from the second fluorescent label; the light source is configured for generating a third excitation light at a third excitation wavelength different from the first excitation wavelength and the second excitation wavelength; the light detector is configured for measuring a third detection signal at a third emission wavelength; and the computing device is configured for: controlling the light source to generate the third excitation light at a predetermined excitation time and for a predetermined duration; and controlling the light detector to measure the third detection signal at a third measurement time.

According to another embodiment, the fluorescence detection apparatus or system includes an apparatus housing, a cartridge removably installed in the apparatus housing, excitation optics configured for defining an optical path from the light source to the sample, and emission optics configured for defining an optical path from the sample to the light detector, wherein: the light source is disposed in the cartridge or in the apparatus housing; the light detector is disposed in the cartridge or in the apparatus housing; and the computing device is disposed in the apparatus housing.

According to another embodiment, a fluorescence detection apparatus or system is configured for performing all or part of any of the methods disclosed herein.

According to another embodiment, an apparatus or system for performing fluorescence detection includes: a processor and a memory configured for performing all or part of any of the methods disclosed herein.

According to another embodiment, a computer-readable storage medium includes instructions for performing all or part of any of the methods disclosed herein.

According to another embodiment, an apparatus or system includes the computer-readable storage medium.

Other devices, apparatuses, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 3A is a schematic view of an example of a fluorescence detection apparatus according to an embodiment.

FIG. 3E is a schematic view of an example of a fluorescence detection apparatus according to another embodiment.

FIG. 3F is a schematic view of an example of a fluorescence detection apparatus according to another embodiment.

FIG. 3G is a schematic view of an example of a fluorescence detection apparatus according to another embodiment.

DETAILED DESCRIPTION

Figure 1:
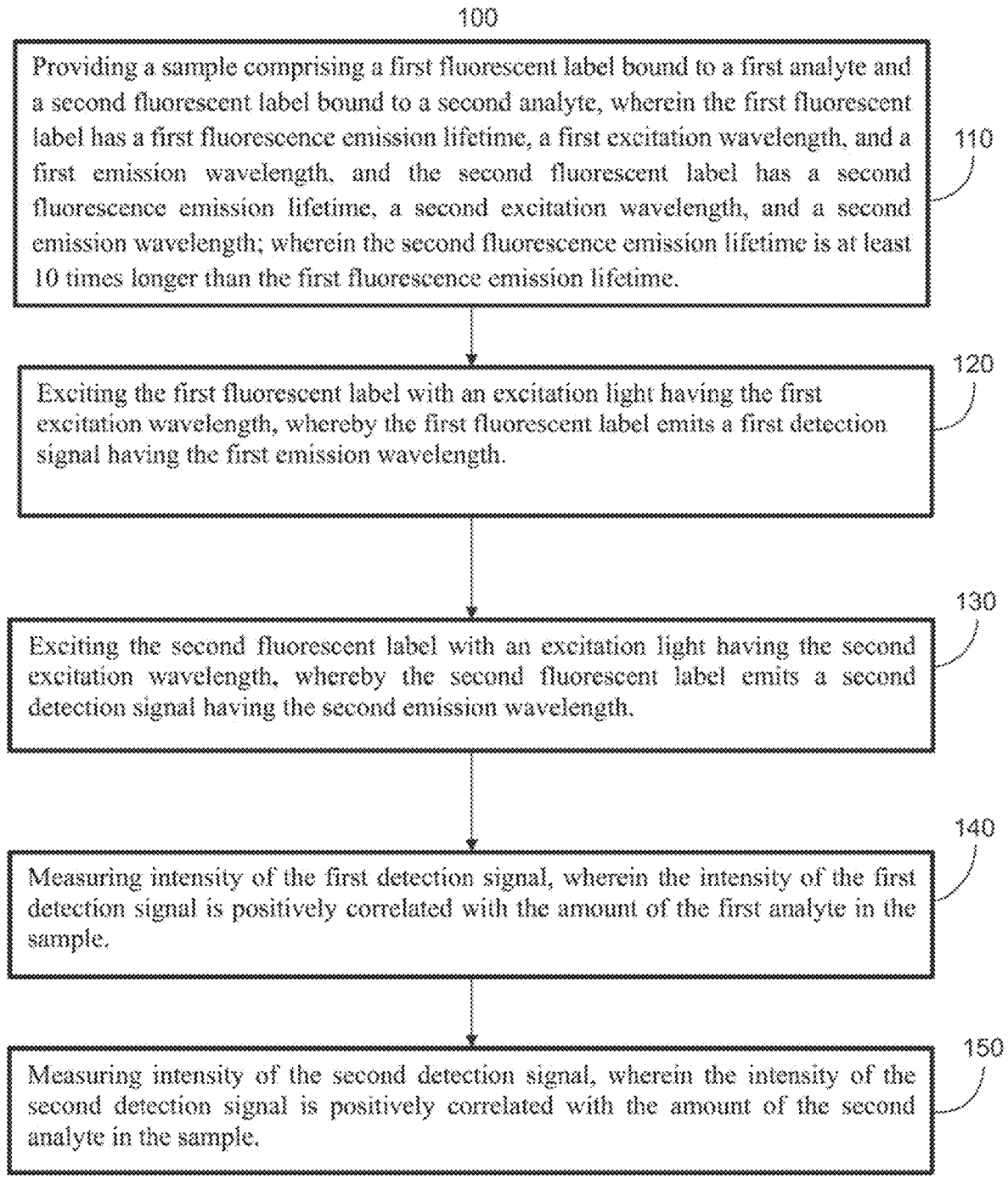
FIG. 1 is a flow chart of a method for multiplexed time-resolved fluorescence (TRF) detection according to some embodiments.

As used herein, the term "analyte" generally refers to a substance to be detected. For example, in other particular embodiments, the first analyte and the second analyte within the method for performing multiplexed TRF detection comprise proteins, more particularly membrane-bound proteins. Analytes may also include antigenic substances, haptens, antibodies, and combinations thereof. Accordingly, analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances.

As used herein, the term "sample" generally refers to a material known or suspected of containing the analyte. The sample may be used directly as obtained from the source or following a pretreatment to modify the character of the sample. The sample may be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The sample may be pretreated prior to use, such as preparing plasma from blood, diluting viscous fluids, and the like. Methods of pretreatment can involve filtration, precipitation, dilution, distillation, concentration, inactivation of interfering components, chromatography, separation steps, and the addition of reagents. Besides physiological fluids, other liquid samples may be used such as water, food products and the like for the performance of environmental or food production assays. In addition, a solid material known or suspected of containing the analyte may be used as the sample. In some instances it may be beneficial to modify a solid sample to form a liquid medium or to release the analyte.

As used herein, the term "light" generally refers to electromagnetic radiation, quantizable as photons. As it pertains to the present disclosure, light may propagate at wavelengths ranging from ultraviolet (UV) to infrared (IR). In the present disclosure, the term "light" is not intended to be limited to electromagnetic radiation in the visible range. In the present disclosure, the terms "light," "photons," and "radiation" are used interchangeably.

The present invention is directed to methods for multiplexing various types of fluorophores, including long-lifetime fluorescent dyes and upconversion phosphors (UCPs), using normal fluorescence detection (FD), time-resolved fluorescence (TRF) detection, or a combination of both. A combination of spectral and temporal differences in fluorescence emission is used to enhance the ability to separate signals in an assay from multiple dyes. Multiplexed fluorescence detection apparatuses and systems configured for performing all or part of any of the methods disclosed herein are also provided, including apparatuses and systems incorporating cartridge-based optical plate readers such as so-called multi-mode readers.

Conventional TRF detection involves exciting a fluorescent label with a short pulse of light, then typically waiting a certain time after excitation before measuring the remaining long-lived fluorescent signal. In this manner, any short-lived fluorescent background signals and scattered excitation radiation are eliminated. This ability to eliminate much of the background signals can result in sensitivities that are 2 to 4 orders greater than conventional fluorescence. Thus, TRF detection is designed to reduce background signals from the emission source or from scattering processes (resulting from scattering of the excitation radiation) by taking advantage of the fluorescence characteristics of certain fluorescent materials.

The typical selection criteria of fluorescent labels for TRF include a relatively long emission lifetime. As indicated above, this is desired so that the label emits its signal well after any short-lived background signals dissipate. A long fluorescence lifetime also makes it possible to use flashlamp excitation and low-cost circuitry for time-gated fluorescence measurements. In addition, the fluorescent label may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of the fluorescent label to remain far apart from its emission wavelengths and is desirable because a large difference between excitation and emission wavelengths makes it easier to eliminate excitation radiation from the emitted signal. Further, a large Stokes shift also minimizes interference from fluorescent molecules in the sample and/or light scattering due to proteins or colloids, which are present with some body fluids (e.g., blood). In addition, a large Stokes shift also minimizes the requirement for expensive, high-precision filters to eliminate background interference.

One type of fluorescent compound that has both a relatively long emission lifetime and relatively large Stokes shift are lanthanide chelates such as chelates of samarium (Sm (III)), dysprosium (Dy(III)), europium (Eu(III)), and terbium (Tb(III)). Such chelates can exhibit strongly red-shifted, narrow-band, long-lived emission after excitation of the chelate at substantially shorter wavelengths. Typically, the chelate possesses a strong ultraviolet (UV) excitation band due to a chromophore located close to the lanthanide in the molecule. Subsequent to excitation by the chromophore, the excitation energy can be transferred from the excited chromophore to the lanthanide. This is followed by a fluorescence emission characteristic of the lanthanide. Lanthanide chelates, for instance, have exceptionally large Stokes shifts of about 250 to about 350 nanometers (nm), as compared to only about 28 nanometers for fluorescein. Also, the fluorescence of lanthanide chelates is long-lived, with lifetimes of about 100 to about 1000 microseconds (µs), as compared to about 1 to about 20 nanoseconds (nm) for other fluorescent labels. In addition, these chelates have a very narrow emission spectra, typically having bandwidths less than about 10 nanometers at about 50% emission.

Another type of fluorescent compound that has both a relatively long emission lifetime and relatively large Stokes shift are transition metal chelates such as chelates of ruthenium (Ru(II)), osmium (Os(II)), and rhenium (Re(I)). The fluorescence lifetime of transition metal chelates is typically about 0.1 to about 10 microseconds.

As described above, the present invention in one aspect is directed to a novel method to multiplex long lifetime fluorescent dyes using TRF detection. A combination of spectral and temporal differences in fluorescence emission is used to enhance the ability to separate signals in an assay from multiple dyes. The method exploits both time-domain and wavelength-domain differences between TRF dyes to reduce cross-talk to below 1%, and more particularly to below 0.01%.

The multiplexed TRF detection methods of the present invention provide a number of advantages compared to conventional methods. For example, improved quantitation may be achieved by using one channel as a reference or standard. For example, when using conventional methods for loading samples into a column on a gel to perform a Western Blot there can be significant error in how much sample actually makes it down the lane. By utilizing a reference protein (also known as a housekeeping protein) signal in one channel, then the signal from an "unknown" protein in a second (or third) channel can be normalized to the reference channel to improve relative accuracy.

Another advantage of the multiplexed TRF detection methods of the present invention is that they allow for improved ratiometric measurements. A common application of Western Blot is to look at phosphorylation of a protein as an indicator of a signaling event and calculate the ratio of phosphoprotein to unmodified (or total) protein. Using single channel Western Blot to calculate such a ratio requires measuring the first protein, stripping the Western Blot membrane, and then re-probing and measuring the second protein. Two-channel detection allows for probing and measurement of both phospho- and total-protein at the same time. This saves significant time and increases accuracy since sources of experimental error are removed by not having to strip and re-probe.

FIG. 1 is a flow chart of a method 100 for multiplexed TRF detection according to some embodiments. First, a sample is provided comprising a first fluorescent label bound to a first analyte and a second fluorescent label bound to a second analyte, wherein the first fluorescent label has a first fluorescence emission lifetime which is at least three (3) times longer than background fluorescence emission lifetimes, a first excitation wavelength, and a first emission wavelength, and the second fluorescent label has a second fluorescence emission lifetime, a second excitation wavelength, and a second emission wavelength, and wherein the second fluorescence emission lifetime is at least five (5) times longer than the first fluorescence emission lifetime (step 110). Next, the first fluorescent label is excited with a first excitation light having the first excitation wavelength, wherein the first fluorescent label emits a first detection signal having the first emission wavelength (step 120). Then, the second fluorescent label is excited with a second excitation light having the second excitation wavelength, wherein the second fluorescent label emits a second detection signal having the second emission wavelength (step 130). Next, intensity of the first detection signal is measured, wherein the intensity of the first detection signal is positively correlated with the amount of the first analyte in the sample (step 140). Then, intensity of the second detection signal is measured, wherein the intensity of the second detection signal is positively correlated with the amount of the second analyte in the sample (step 150). In particular embodiments, the second fluorescence emission lifetime is at least 100 times or at least 1,000 times longer than the first fluorescence emission lifetime.

In some embodiments, the flow chart of FIG. 1 may be considered as schematically representing a sample analyzing apparatus configured for carrying out all or part of the steps of the method 100 described above. Further examples of a sample analyzing apparatus are described below.

In other particular embodiments, the method for performing multiplexed TRF detection comprises the use of a second fluorescent label having a second fluorescence emission lifetime in a range of 100 μs to 1 ms, more particularly wherein the second fluorescent label is selected from the group consisting of lanthanide chelates of samarium (Sm (III)), dysprosium (Dy(III)), europium (Eu(III)), and terbium (Tb(III)). In further particular embodiments, the method for performing multiplexed TRF detection comprises the use of a first fluorescent label having a first fluorescence emission lifetime in a range of 0.1 μs to 10 μs, more particularly wherein the first fluorescent label is selected from the group consisting of transition metal chelates of ruthenium (Ru(II)), osmium (Os(II)), and rhenium (Re(I)).

In further particular embodiments, the fluorescent labels within the method for performing multiplexed TRF detection have a Stokes shift of greater than about 20 nanometers, in some embodiments greater than about 100 nanometers, and in some embodiments from about 250 to about 350 nanometers.

In further embodiments, prior to step 110 the sample is prepared according to the following steps:
a) contacting the sample with:
  i) a first antibody that specifically binds the first analyte;
  ii) a second antibody that specifically binds the second analyte;
  iii) a first fluorescent antibody conjugate that specifically binds the first antibody, wherein the first fluorescent antibody conjugate comprises a first fluorescent label having a first fluorescence emission lifetime, a first excitation wavelength, and a first emission wavelength;
  iv) a second fluorescent antibody conjugate that specifically binds the second antibody, wherein the second fluorescent antibody conjugate comprises a second fluorescent label having a second fluorescence emission lifetime, a second excitation wavelength, and a second emission wavelength; and
b) incubating the sample under conditions and for a time sufficient to allow the antibodies and the antibody conjugates to form immunocomplexes. In some embodiments, the antibodies and antibody conjugates may be provided in the form of a mixture in solution, or the antibodies and/or antibody conjugates may be attached to the surface of a solid support. The solid support may be, but is not limited to, magnetic beads, gold nanoparticles, biodegradable organic polymer nanoparticles, microwells, or microtiter plates. In other embodiments, the first or second antibodies may have the first or second fluorescent labels directly attached to them eliminating the need for antibody conjugates. Accordingly, the presently disclosed methods encompass a wide range of assays for the detection of analytes, such as the detection of proteins bound to membranes, proteins bound to beads, proteins in microfluidic channels (potentially separated), proteins in the wells of a multi-well plate, and/or proteins in gels or other viscous media (potentially separated).

In other particular embodiments, the sample within the method for performing multiplexed TRF detection comprises at least one additional fluorescent label bound to an additional analyte. The additional fluorescent label has a label-specific excitation wavelength, a label-specific emission wavelength, and a label-specific fluorescence emission lifetime which may be at least 3 times longer than background emission lifetimes. Furthermore, the first fluorescence emission lifetime, the second fluorescence emission lifetime, and the label-specific fluorescence emission lifetime each may be at least an order of magnitude different from one another. The additional fluorescent label is excited with a label-specific excitation light having the label-specific excitation wavelength, whereby the additional fluorescent label emits a label-specific detection signal having the label-specific emission wavelength. Intensity of the label-specific detection signal is then measured, wherein the intensity of the label-specific detection signal is positively correlated with the amount of the additional analyte in the sample. The at least one additional fluorescent label bound to an additional analyte may also comprise a plurality of different fluorescent labels bound to different analytes.

In a further embodiment, within the method for performing multiplexed TRF detection, the first analyte is a reference protein and the second analyte is an unknown protein, further wherein the second detection signal is normalized to the first detection signal.

In another embodiment, within the method for performing multiplexed TRF detection, the first analyte is a protein and the second analyte is a modified version of the protein, further wherein the ratio of modified protein to unmodified protein is calculated, particularly wherein the modified version of the protein is a phosphorylated version of the protein.

In further embodiments, one or more upconversion phosphors (UCPs) may be utilized as fluorescent labels, and may be utilized in combination with other types of fluorescent labels (i.e., "non-UCP" labels) such as the lanthanide chelates and transition metal chelates described herein. As appreciated by persons skilled in the art, a UCP exhibits an anti-Stokes shift (or negative Stokes shift) rather than a positive Stokes shift. That is, in the process of photon upconversion, the sequential absorption of two or more photons of excitation light by a UPC results in emission of light by the UPC at a shorter wavelength than the excitation wavelength, rather than at a longer wavelength than the excitation wavelength. In a typical example, a UPC emits emission light in the visible spectrum (e.g., 600 nm) in response to absorbing light in the infrared (IR) spectrum (e.g., 980 nm). Like the non-UCP fluorescent labels described herein, UCP fluorescent labels can be configured (formulated, fabricated) to have prolonged emission lifetimes. Moreover, the IR wavelengths at which UCP fluorescent labels are irradiated are significantly different (i.e., far separated spectrally) from the UV wavelengths at which the non-UCP fluorescent labels are irradiated, and enables background noise to be reduced significantly. The emission wavelengths of UCP labels are also sufficiently different from the non-UCP labels to provide very good resolution in the measurement signals and very reduced cross-talk. According to an aspect of the present disclosure, the use of different labels, such as a UCP label and one or more different non-UCP labels, entails the use of different excitation wavelengths, different emission wavelengths, and different emission lifetimes, resulting in very little cross-talk. As in the case of the non-UCP labels, the specific excitation wavelengths, emission wavelengths, and emission lifetimes depend on the particular configuration of a given UCP. Combining the use of one or more UCP labels with one or more non-UCP labels (e.g., lanthanide chelates and/or transition metal chelates) in multiplexed (e.g., duplex, triplex, etc.) experiments may also reduce the amounts of sample experimental time required. In addition, certain UCP labels are useful for normal fluorescence-based experiments, i.e., simultaneously detecting/measuring a sample while irradiating the sample (i.e., with little or no delay required between excitation and detection/measurement of emission), due to very low background signal associated with UCPs. Thus, in some embodiments disclosed herein, the method when utilizing such UCPs in combination non-UCP labels with may entail TRF or a combination of normal fluorescence and TRF.

As a non-limiting example, the UCP may be a lanthanide-doped or transition metal-doped inorganic compound exhibiting anti-Stokes shift. The inorganic compound may be a crystalline material that includes a transparent host lattice doped with one or more dopants that enable or enhance the upconversion activity. Examples of inorganic compounds forming the basis for certain UCPs include, but are not limited to, various halides (e.g., $NaYF_4$, $YF_3$, $LaF_3$), oxides (e.g., $Y_2O_3$, $ZrO_2$), and oxysulfides (e.g., $Y_2O_2S$, $La_2O_2S$). Examples of suitable dopants include, but are not limited to, trivalent lanthanide ions and transition metals such as erbium ($Er^{3+}$), thulium ($Tm^{3+}$), holmium ($Ho^{3+}$), praseodymium ($Pr^{3+}$), neodymium ($Nd^{3+}$), dysprosium ($Dy^{3+}$), ytterbium ($Yb^{3+}$), and/or samarium ($Sm^{3+}$). As another example, UCPs may be utilized as described by Riuttamaki, Terhi, *UPCONVERTING PHOSPHOR TECHNOLOGY: Exceptional Photoluminescent Properties Light Up Homogeneous Bioanalytical Assays*, University of Turku Publications (2011), the entire content of which is incorporated by reference herein. As another example, suitable UCPs may be SUNSTONE® UCP Nanocrystals manufactured by Intelligent Material Solutions Inc., Princeton, N.J., USA, and commercially available from Sigma-Aldrich, Inc., St. Louis, Mo., USA.

Methods disclosed herein may be implemented with the use of a suitable sample analyzing apparatus. Examples of suitable sample analyzing apparatuses are described below with reference to FIGS. 2 to 3H.

Figure 2:
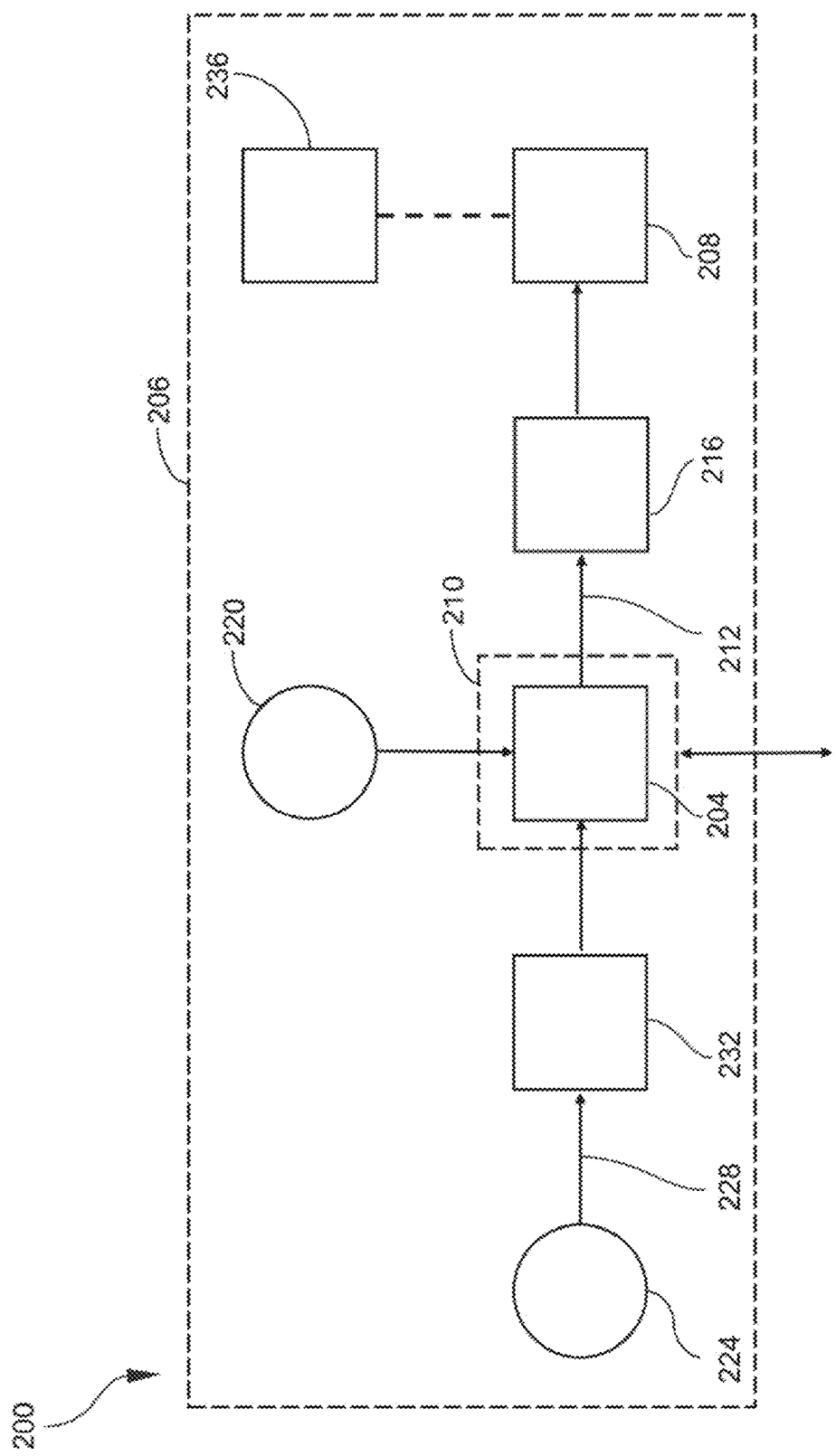
FIG. 2 is a schematic view of an example of a sample analyzing apparatus according to some embodiments.

FIG. 2 is a schematic view of an example of a sample analyzing according to some embodiments. The sample analyzing apparatus 200 is configured for performing multiplexed fluorescence detection on a sample to detect multiple analytes, as these terms have been defined elsewhere herein. In some embodiments, the sample analyzing apparatus 200 is configured to enable a user to select a desired type of optical measurement to be performed, not only TRF measurement but other fluorescence-based measurements as well as other types of optical measurements such as, for example, luminescence, absorbance, cell imaging, etc. For example, the user may be able to reconfigure the optics of the sample analyzing apparatus 200 to perform a desired type of fluorescence measurement. Thus, in some embodiments the sample analyzing apparatus 200 may be a multi-mode reader. For example, as a multi-mode reader the sample analyzing apparatus 200 may be reconfigurable by enabling a user to select an application-specific cartridge among a number of different cartridges available, and load the selected cartridge into the sample analyzing apparatus 200 so as to establish optical and electrical circuits specific to the desired application. The selected cartridge is coupled to the sample analyzing apparatus 200 whereby the sample analyzing apparatus 200 is properly configured for carrying out the selected experiment. The cartridge may contain optics specific to or optimized for a particular type of application such as, for example, multiplexed TRF detection. The internal optics housed within the cartridge may communicate with external optics housed within the housing of the sample analyzing apparatus 200 through optical ports of the cartridge's housing. Some cartridges may additionally include one or more internal light sources and/or one or more light detectors. Examples of cartridge-based multi-mode readers are described in U.S. Pat. Nos. 9,188,527 and 8,119,066, the contents of which are incorporated by reference herein in their entireties.

Generally, the structure and operation of the various components provided in optical-based sample analysis instruments are understood by persons skilled in the art, and thus are only briefly described herein to facilitate an understanding of the presently disclosed subject matter. In the illustrated embodiment, the sample analyzing apparatus 200 includes a sample support 204 configured for supporting one or more samples under analysis, and a light detector 208 configured for receiving and measuring emitted light 212 emitted from the sample. The sample support 204 when in an operative position for carrying out optical measurements on the sample, and the light detector 208 and other components illustrated in FIG. 2, may be enclosed in an apparatus housing 206 of the sample analyzing apparatus 200. The apparatus housing 206 may include one or more panels, doors, drawers, etc. for loading the sample support 204 (and cartridges if provided), accessing interior regions of the sample analyzing apparatus 200, etc.

Generally, the sample support 204 may be one or more containers configured for holding one or more samples during an analysis. As non-limiting examples, the sample support 204 may be a multi-well plate (also known as a microtiter plate, microplate, or optical plate), one or more cuvettes, a substrate supporting spots or blots containing respective samples, etc. The sample support 204 may be disposed on a sample carrier (or sample support carrier) 210 configured for moving the sample support 204 along more or more axes. For example, the sample carrier 210 may be a manually actuated, semi-automated, or motorized stage or platform. The sample carrier 210 may be movable into and out from the apparatus housing 206, as indicated by an arrow in FIG. 2. A sample, or the sample support 204 containing one or more samples, may be mounted onto the sample carrier 210 while the sample carrier 210 is at an outside position, e.g., where the sample carrier 210 is positioned at least partially outside the apparatus housing 206. The sample carrier 210 may thus also be considered as a sample support. The sample carrier 210 may then be moved to an inside position at which the sample carrier 210 is positioned entirely in the apparatus housing 206 so as to align the sample (or successively align multiple samples) with an optical component and/or liquid handling component of the sample analyzing apparatus 200

In various embodiments, the optical input end of the light detector 208 typically includes a lens. The output end may include an electrical connector (e.g., contacts, terminals, pins, wire support, etc.) to provide power and enable measurement signals generated by the light detector 208 to be outputted to signal processing circuitry (e.g., data acquisition circuitry) provided with or external to the sample analyzing apparatus 200. Depending on the embodiment, the light detector 208 may be a photomultiplier tube (PMT), a photodiode, a charge-coupled device (CCD), an active-pixel sensor (APS) such as a complementary metal-oxide-semiconductor (CMOS) device, etc., as needed to optimize sensitivity to the emission wavelengths to be detected.

In typical embodiments, the sample analyzing apparatus 200 further includes emission optics 216 configured for transmitting the emitted light 212 from the sample to the light detector 208. The emission optics 216 may also be configured for processing the emitted light 212. Examples of processing include, but are not limited to, collecting, focusing, collimating, filtering, beam steering, beam splitting, and optical path switching. Thus, depending on the embodiment, the emission optics 216 may include one or more lenses, read heads, apertures, filters, light guides, mirrors, beam splitters, monochromators, diffraction gratings, prisms, optical path switches, etc. The emission optics 216 may configured for receiving emitted light 212 from above the sample (e.g., a top read head) and/or below the sample (e.g., a bottom read head).

In some embodiments, the sample analyzing apparatus 200 further includes a liquid dispensing system 220 (e.g., injector needle(s), tubing, pump(s), reservoir(s), etc.) configured for adding a liquid to the sample (e.g., into selected wells or onto selected blots of the sample support 204) before or after the sample has been operatively positioned in the sample analyzing apparatus 200. For example, a labeling agent may be added to the sample for fluorescence, luminescence or other types of measurements, as appreciated by persons skilled in the art. In some embodiments, two or more different types of reagents may be added.

In embodiments requiring excitation such as the fluorescence detection techniques disclosed herein, the sample analyzing apparatus 200 includes one or more light sources 224 for producing excitation light 228 of a desired wavelength that is directed to the sample. Depending on the embodiment, the light source 224 may include a broadband light source (e.g., flash lamp) or one or more light emitting diodes (LEDs), laser diodes (LDs), lasers, etc. Multiple light sources 224 may be provided to enable a user to select a desired excitation wavelength. In typical embodiments, the sample analyzing apparatus 200 further includes excitation optics 232 configured for transmitting the excitation light 228 from the light source 224 to the sample. The excitation optics 232 may include, for example, one or more lenses, read heads, apertures, filters, light guides, mirrors, beam splitters, monochromators, diffraction gratings, prisms, optical path switches, etc., as noted above.

In embodiments in which the light source 224 is an LED light source, the sample analyzing apparatus 200 (or a cartridge operatively coupled to the sample analyzing apparatus 200) may have an electronic current supply that is capable of pulsing the LED light source, a control for changing the intensity of the exciting light from the LED light source, and/or a photodiode that is capable of measuring the intensity of exciting light produced by the LED light source, which may be used to stabilize the LED light source. Preferred LED light sources are obtained from Lumileds, San Jose, Calif.; Luxeon Star, Nichia, Tokushima, Japan; and Roithner-Laser, Vienna, Austria. In other embodiments, the light source 224 may be a Xenon flash lamp module, the module having a Xenon flash lamp as the light source and having the corresponding electronics to produce a pulsed light beam. In the case of using a wide band light source, such as a Xenon flash lamp, the optical system includes a wavelength selector, filter, or the like for controlling the wavelength of the exciting light. Preferred Xenon flash lamp modules are obtained from Excelitas, Waltham, Mass.; and Hamamatsu Photonics, Japan.

As also schematically illustrated in FIG. 2, the sample analyzing apparatus 200 may further include a computing device (or system controller) 236. As appreciated by persons skilled in the art, the computing device 236 may represent one or more modules configured for controlling, monitoring and/or timing various functional aspects of the sample analyzing apparatus 200, and/or for receiving data or other signals from the sample analyzing apparatus 200 such as measurement signals from the light detector 208 and transmitting control signals to the light detector 208 and/or other components. For all such purposes, the computing device 236 may communicate with various components of the sample analyzing apparatus 200 via wired or wireless communication links, as depicted by a dashed line between the computing device 236 and the light detector 208. For simplicity, other communication links that may be present between the computing device 236 and other components of the sample analyzing apparatus 200 are not shown. In typical embodiments, the computing device 236 includes a main electronic processor providing overall control, and may include one or more electronic processors configured for dedicated control operations or specific signal processing tasks. The computing device 236 may also include one or more memories and/or databases for storing data and/or software. The computing device 236 may also include a computer-readable medium 236 that includes instructions for performing any of the methods disclosed herein. The functional modules of the computing device 236 may comprise circuitry or other types of hardware (or firmware), software, or both. For example, the modules may include signal processing (or data acquisition) circuitry for receiving measurement signals from the light detector 208 and software for processing the measurement signals such as for generating graphical data. The computing device 236 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The computing device 236 may include an operating system (e.g., Microsoft Windows® software) for controlling and managing various functions of the computing device 236.

According to some embodiments, an experiment entailing optical measurement utilizing the analyzing apparatus 200 may be implemented as follows. The sample is introduced into the sample analyzing apparatus 200 and placed in a proper operating position relative to optics and other components of the sample analyzing apparatus 200. Generally, the "operating" position of the sample is an "optically aligned" position, i.e., a position that establishes an optical path sufficient for optical data acquisition from the sample. Depending on the experiment, the operating position may also correspond to the sample being "fluidly aligned" with the sample analyzing apparatus 200, i.e., positioned so as to be able to dispense fluid onto the sample such as by operating the liquid dispensing system 220. Sample introduction may entail loading one or more samples in one or more wells of a microplate or other type of sample support 204 (e.g., preparing samples in accordance with botting techniques such as Western Blot, as appreciated by persons skilled in the art), and loading or mounting the sample support 204 in the sample analyzing apparatus 200, such as with the use of a sample carrier 210 as noted above. Also as noted above, depending on the sample and the type of measurement to be made, the sample may be subjected to preparation or treatment (incubation, mixing, homogenization, centrifuging, buffering, reagent addition, analytical separation such as solid phase extraction, chromatography, electrophoresis, etc.) prior to being positioned in the sample analyzing apparatus 200, as appreciated by persons skilled in the art.

In addition to sample introduction, the sample analyzing apparatus 200 or certain components thereof (optics, electronics, etc.) may need to be configured for implementing the specific type of measurement to be made. For example, if cartridge-based, the appropriate cartridge (or cartridges) may be installed in the sample analyzing apparatus 200. After installing a cartridge, optics provided in the cartridge become part of the optical circuit within the housing 206 of the sample analyzing apparatus 200. For example, the cartridge optics may be aligned with (in optical communication with) the emission optics 216 and light detector 208, and in some embodiments also with the excitation optics 232 and light source 224. Installing the cartridge results in establishing electrical paths for transmitting power, data and control signals to and/or from the cartridge.

The sample is then processed as necessary to induce the emission of photons from the sample which, for fluorescence, may entail the addition of reagents using the liquid dispensing system 220 and/or irradiation/excitation using the light source 224 and associated excitation optics 232. The emission optics 216 collect the emitted light 212 from the sample and direct the emitted light 212 to the light detector 208. The light detector 208 converts these optical signals into electrical signals (detector signals, or measurement signals) and transmits the electrical signals to signal processing circuitry, such as may be provided by a computing device 236 of the sample analyzing apparatus 200 as described above. In the case of multiple samples, the sample support 204 may be moved (such as by using a sample carrier 210 as described above) to sequentially align each additional sample with the optics being utilized for the experiment, whereby measurements are taken from all samples sequentially.

As noted above, the sample analyzing apparatus 200 may be utilized to carry out all or part of any of the methods disclosed herein. Accordingly, the sample analyzing apparatus 200 may also be referred to as a fluorescence detection apparatus. For example, the light source 224 may be operated to irradiate the sample with a first excitation signal having a first excitation wavelength optimized for exciting a first fluorescent label of the sample, and with a second excitation signal having a second excitation wavelength optimized for exciting a second fluorescent label of the sample. The light detector 208 may be operated to measure a first detection signal emitted from the sample at a first emission wavelength in response to excitation by the first excitation signal, and a second detection signal emitted from the sample at a second emission wavelength in response to excitation by the second excitation signal. For these purposes, in some embodiments the light source 224 may include at least two discrete light sources and/or the light detector 208 may include at least two discrete light detectors.

According to another embodiment, an apparatus for multiplexed fluorescence detection (or a multiplexed fluorescence detection apparatus) is provided. Referring now to FIG. 3A, an apparatus 300 for multiplexed fluorescence detection is shown. A sample 332 may be held within the apparatus 300 on a sample support 334, such as a microplate or a membrane or substrate supporting samples. The apparatus 300 comprises a first light source 310 that produces a first excitation light 320 and a second light source 312 that produces a second excitation light 322. The apparatus 300 has a first excitation light optical system 324 and a second excitation light optical system 326, which have components for directing the first excitation light 320 and second excitation light 322, respectively, to the sample 332 as described above in conjunction with FIG. 2. The sample 332, containing a first analyte 330 and a second analyte 331, emits a first emitted light 340 and a second emitted light 342. The apparatus 300 has a first emitted light optical system 344 which receives the first emitted light 340 and a second emitted light optical system 346 which receives the second emitted light 342. The first emitted light optical system 344 then directs the first emitted light 340 to a first detector 350, and the second emitted light optical system 346 then directs the second emitted light 342 to a second detector 352. The foregoing components may be positioned in a main apparatus housing of the apparatus 300 (e.g., the apparatus housing 206 illustrated in FIG. 2).

Figure 3B:
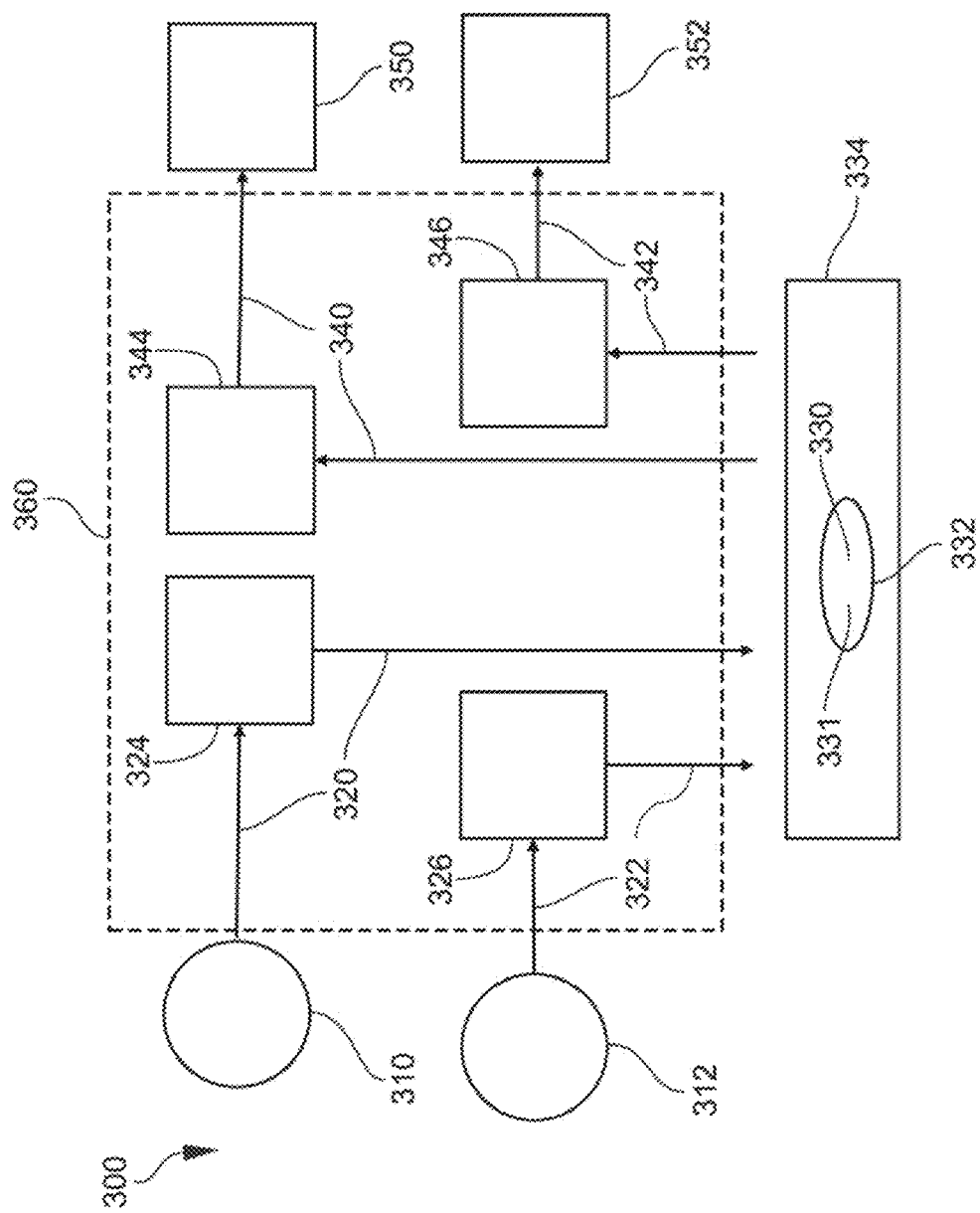
FIG. 3B is a schematic view of an example of a fluorescence detection apparatus according to another embodiment.

FIGS. 3B through 3H are schematic views of components of the apparatus 300 illustrated in FIG. 3A, in which various components of the apparatus 300 are illustrated as contained inside or outside of one or more cartridges according to some embodiments. That is, such a cartridge may generally include a cartridge housing that encloses (contains) one or more components of the apparatus 300. Such cartridge(s)

may be loaded or installed in the apparatus 300 such that the cartridge(s) are enclosed in the interior of a main apparatus housing of the apparatus 300 (e.g., the apparatus housing 206 illustrated in FIG. 2). Examples of cartridge-based readers are described in above-referenced U.S. Pat. Nos. 9,188,527 and 8,119,066.

Referring now to FIG. 3B, the apparatus 300 further comprises a cartridge 360 comprising the first excitation light optical system 324, the second excitation light optical system 326, the first emitted light optical system 344, and the second emitted light optical system 346.

Figure 3C:
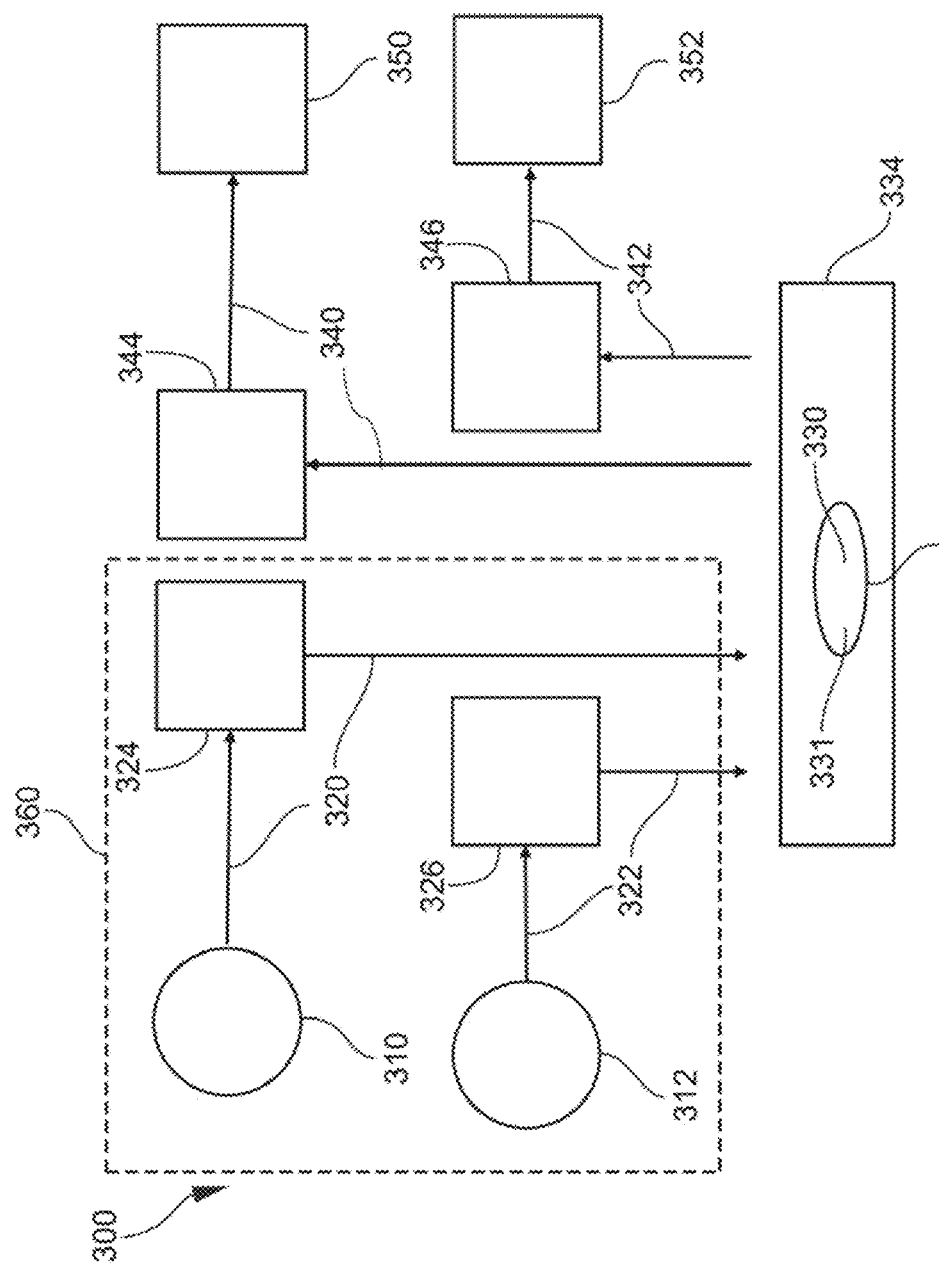
FIG. 3C is a schematic view of an example of a fluorescence detection apparatus according to another embodiment.

Referring now to FIG. 3C, the apparatus 300 further comprises a cartridge 360 comprising the first light source 310, the second light source 312, the first excitation light optical system 324, and the second excitation light optical system 326.

Figure 3D:
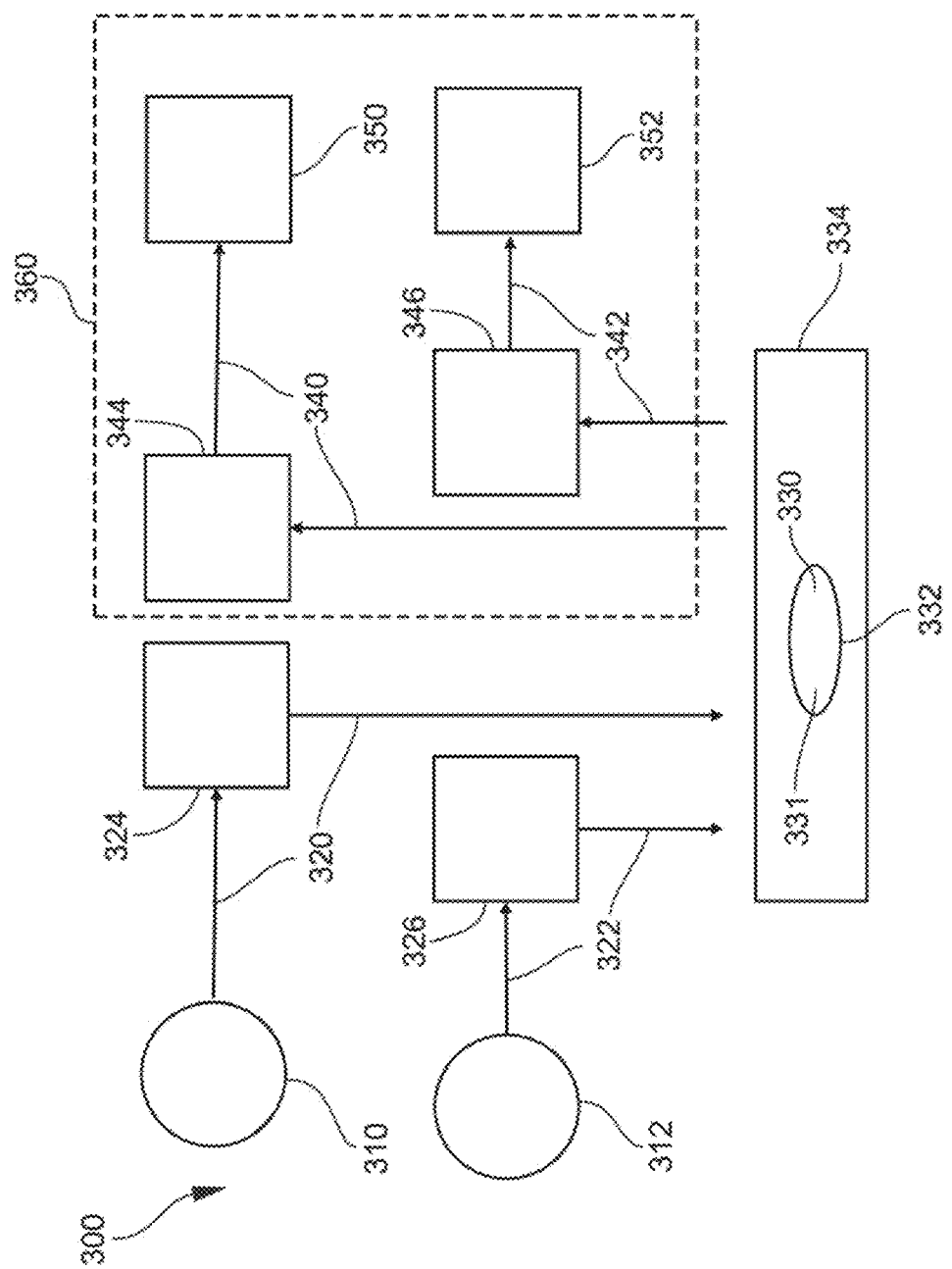
FIG. 3D is a schematic view of an example of a fluorescence detection apparatus according to another embodiment.

Referring now to FIG. 3D, the apparatus 300 further comprises a cartridge 360 comprising the first emitted light optical system 344, the second emitted light optical system 346, the first detector 350, and the second detector 352.

Referring now to FIG. 3E, the apparatus 300 further comprises a cartridge 360 comprising the first excitation light optical system 324, the first light source 310, the first emitted light optical system 344, and the first detector 350.

Referring now to FIG. 3F, the apparatus 300 further comprises a cartridge 360 comprising the first light source 310, the second light source 312, the first excitation light optical system 324, the second excitation light optical system 326, the first emitted light optical system 344, the second emitted light optical system 346, the first detector 350, and the second detector 352.

Referring now to FIG. 3G, the apparatus 300 further comprises a first cartridge 360 comprising the first light source 310, the first excitation light optical system 324, the first emitted light optical system 344, and the first light detector 350. The apparatus 300 further comprises a second cartridge 370 comprising the second light source 312, the second excitation light optical system 326, the second emitted light optical system 346, and the second light detector 352. In alternative embodiments, the first cartridge 360 may not contain both the first light source 310 and the first light detector 350 as shown, and in further embodiments both the first light source 310 and the first light detector 350 may be external to the first cartridge 360. Likewise, the second cartridge 370 may not contain both the second light source 312 and the second light detector 352 as shown, and in further embodiments both the second light source 312 and the second light detector 352 may be external to the second cartridge 370.

It will be understood to one of skill in the art that, for methods of fluorescence detection involving at least one additional fluorescent label bound to an additional analyte, apparatuses and systems will be configured for performing excitation and detection of the additional fluorescent label. For example, an additional light source configured for generating the label-specific excitation light at the label-specific excitation wavelength could be used, as well as an additional light detector configured for measuring the label-specific detection signal emitted from the sample in response to excitation by the label-specific excitation light. Where the at least one additional fluorescent label bound to an additional analyte comprises a plurality of different fluorescent labels bound to different analytes, a plurality of different additional light sources and light detectors could be used.

Figure 3H:
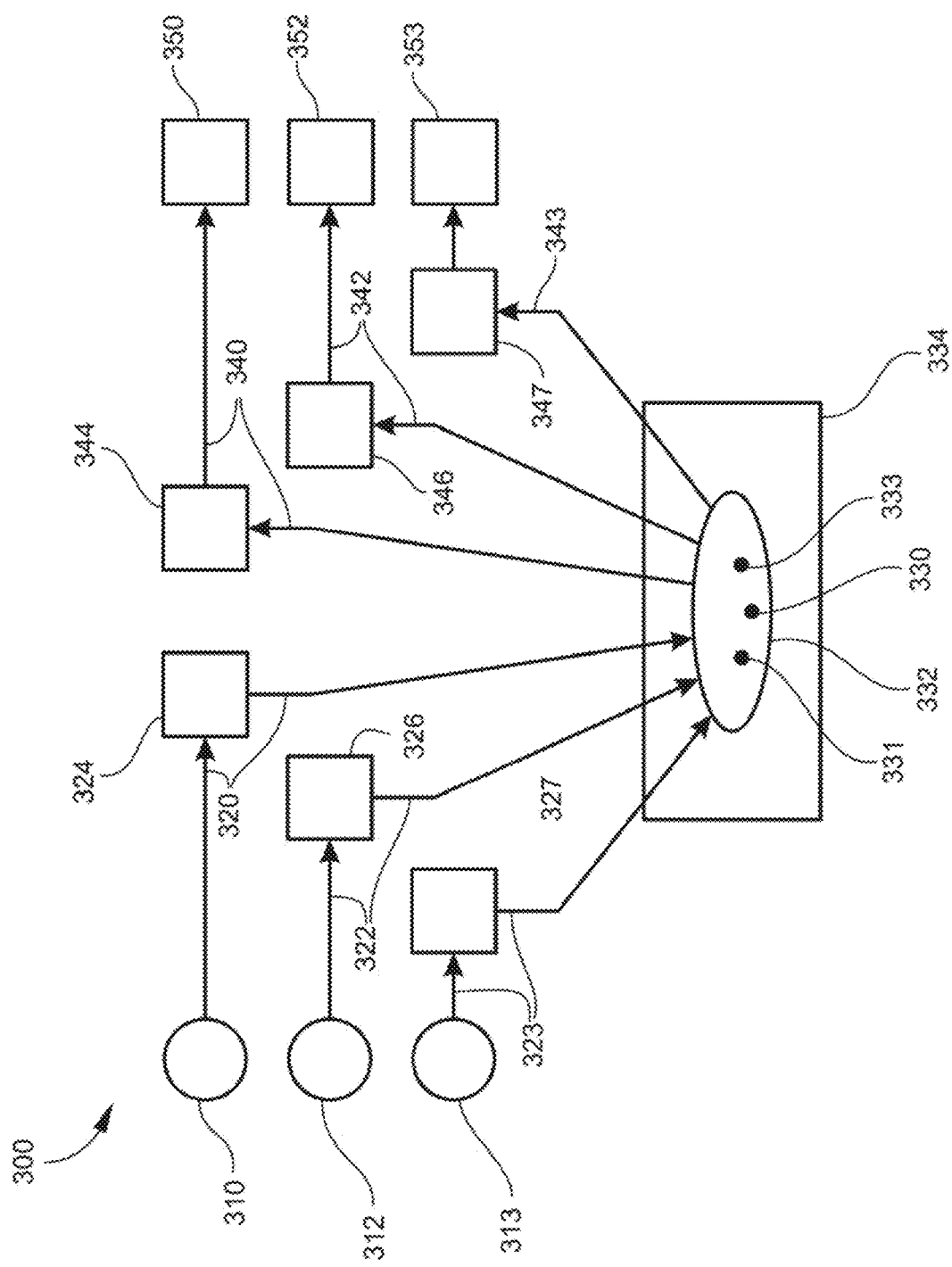
FIG. 3H is a schematic view of an example of a fluorescence detection apparatus according to another embodiment.

As an example, in the embodiment illustrated in FIG. 3H the apparatus 300 may include, in addition to the first light source 310 and the second light source 312 configured for generating the first excitation light 320 and the second excitation light 322, respectively, a third light source 313 configured for generating a third excitation light 327. The apparatus 300 may also include, in addition to the first light detector 350 and the second light detector 352 configured for receiving and measuring a first detection signal 340 and a second detection signal 342 emitted from the first analyte 330 and the second analyte 331, respectively, a third light detector 353 configured for receiving and measuring a third detection signal 343 emitted from a third analyte 333 of the sample 332. The apparatus 300 may also include, in addition to the first excitation optics 324 and the second excitation optics 326, third excitation optics 327. The apparatus 300 may also include, in addition to the first emission optics 344 and the second emission optics 346, third emission optics 347.

As in other embodiments described herein, one or more of the foregoing components may be provided in one or more cartridges (not shown) that may be removably installed in the apparatus 300. As in other embodiments described herein, the apparatus 300 shown in FIG. 3H may be utilized for duplex measurements that employ two different fluorescent labels bound to different analytes. In addition, the apparatus 300 shown in FIG. 3H may be utilized for triplex measurements that employ three different fluorescent labels bound to different analytes. In other embodiments, the apparatus 300 may include more than three light sources and/or more than three light detectors.

As in other embodiments described herein, the apparatus 200 may further include a computing device, such as the computing device (or system controller) 236 described above and schematically illustrated in FIG. 2, which is configured for controlling, monitoring and/or timing various functional aspects of the apparatus 300, receiving data or other signals from the apparatus 300 such as detection signals from the light detectors and transmitting control signals to the light detector detectors and/or other components. For example, in a duplex experiment the computing device may be configured for controlling the first light source 310 and the second light source 312 to respectively generate the first excitation light 320 and the second excitation light 322 at predetermined excitation times and for predetermined durations, controlling the first light detector 350 to measure the first detection signal 340 at a first measurement time, and controlling the second light detector 352 to measure the second detection signal 342 at a second measurement time different from the first measurement time. The computing device may also be configured for receiving an electrical output from the respective light detectors 350 and 352 corresponding to measurements of the first detection signal 340 and the second detection signal 342, and correlating the measurements with the amount of the first analyte 330 in the sample 332 and the amount of the second analyte 331 in the sample 332. The computing device may also be configured for controlling the second light source 312 to cease generating the second excitation light 322, and controlling the second light detector 352 to measure the second detection signal 342 after ceasing generating the second excitation light 322.

As another example, in a triplex experiment the computing device may be configured for controlling the third light source 313 to generate the third excitation light 323 at a predetermined excitation time and for a predetermined duration, and controlling the third light detector 353 to measure the third detection signal 343 at a third measurement time different from the first measurement time and the second measurement time. The computing device may also be configured for controlling the third light source 313 to cease generating the third excitation light 323, and controlling the third light detector 353 to measure the third detection signal 343 at a third measurement time different from the first measurement time and the second measurement time after ceasing generating the third excitation light 323. The computing device may also be configured for receiving an electrical output from the third light detector 353 corresponding to a measurement of the third detection signal 343, and correlating the measurement with the amount of the third analyte 333 in the sample 332.

In any of the embodiments illustrated in FIGS. 2-3H, certain components of the apparatus 300 may be common to (or shared by) more than one channel. Thus, the number of light sources provided may be different from the number of light detectors provided, or the number of sets of excitation or emission optics, etc. For example, a light detector may have a range of wavelength sensitivity that allows it to be effective in detecting signals transmitted over two or more channels. As another example, the emission optics may include an emission filter having a wavelength bandpass effective for filtering detection signals transmitted over two or more channels. Providing common or shared components may reduce the total number of, and total space required by, components required for the apparatus 300, and may enable the apparatus 300 and/or cartridges utilized with the apparatus 300 to be more compact.

An example of a method for multiplexed fluorescence detection according to a representative embodiment will now be described. Reference is made primarily to FIG. 3H as illustrating an example of a fluorescence detection apparatus 300 that may be utilized to implement the method, with the understanding that other apparatuses or systems described herein may also be configured to implement the method.

According to the method, a sample 332 to be analyzed is provided. The sample 332 may include a first fluorescent label bound to a first analyte 330 and a second fluorescent label bound to a second analyte 331. The first fluorescent label may be or include an upconverting phosphor (UCP) label and the second fluorescent label may be or include a non-UCP label. As described herein, the UCP label may be or include a lanthanide-doped or transition metal-doped inorganic compound exhibiting anti-Stokes shift, and non-UCP label may be or include a transition metal chelate or a lanthanide chelate exhibiting (positive) Stokes shift. As non-limiting examples, the Stokes shift of the non-UCP label may be greater than 20 nm, or greater than 100 nm, or greater than 250 nm, or in a range from about 250 nm to about 350 nm.

In some embodiments and as described elsewhere herein, the sample 332 may be provided by contacting the sample 332 with: a first antibody that specifically binds the first analyte 330; a second antibody that specifically binds the second analyte 331; a first fluorescent antibody conjugate that specifically binds the first antibody, the first fluorescent antibody conjugate being or including the first (UCP) fluorescent label; and a second fluorescent antibody conjugate that specifically binds the second antibody, the second fluorescent antibody conjugate being or including the second (non-UCP) fluorescent label. The sample 332 may then be incubated under conditions and for a time sufficient to allow the antibodies and the antibody conjugates to form immunocomplexes.

In other embodiments and as described elsewhere herein, the sample 332 may be provided by contacting the sample 332 with a first antibody that specifically binds the first analyte and a second antibody that specifically binds the second analyte. The first fluorescent label may be attached directly to the first antibody, and/or the second fluorescent label may be attached directly to the second antibody.

The first fluorescent label is irradiated with a first excitation light 320 at a first excitation wavelength. In response, the first fluorescent label emits a first detection signal 340 at a first emission wavelength. The second fluorescent label is irradiated with a second excitation light 322 at a second excitation wavelength that is different from the first excitation wavelength. In response, the second fluorescent label emits a second detection signal 342 at a second emission wavelength which may be different from the first emission wavelength. In the present embodiment, the first excitation wavelength may be in the near-infrared range, and the first emission wavelength may be in the visible range. The second excitation wavelength is in the ultraviolet range, and the second emission wavelength is longer than the second excitation wavelength. Irradiation of the first fluorescent label and irradiation of the second fluorescent label may be done simultaneously or sequentially.

An intensity of the first detection signal 340 is measured at a first measurement time. Irradiation of the second fluorescent label is ceased, after which an intensity of the second detection signal 342 is measured at a second measurement time, which may be different from the first measurement time. The intensity of the first detection signal 340 is correlated with the amount of the first analyte 330 in the sample 332, and the intensity of the second detection signal 342 is correlated with the amount of the second analyte in the sample 332. The emission optics 344, 346 and 347 may be configured to direct the first detection signal 340 and the second detection signal 342 through a common emission filter or through different emission filters.

In some embodiments and as described elsewhere herein, the UCP label, whether or not it has a prolonged emission lifetime, is suitable for taking a reading (making a measurement) according to the normal fluorescence technique. In such case, the intensity of the first detection signal 340 may be measured while irradiating the first fluorescent label. In other embodiments and as described elsewhere herein, the UCP label has a prolonged emission lifetime that is exploited by taking a reading according to the TRF technique. In such case, irradiation of the first fluorescent label is ceased, after which an intensity of the first detection signal is measured. In either case, the first measurement time and the second measurement time may be different from each other. Moreover, the first fluorescence emission lifetime (of the UCP label) and the second fluorescence emission lifetime (of the non-UCP label) may be different from each other. As non-limiting examples, the second fluorescence emission lifetime may be in a range of 0.1 µs to 10 µs, or in a range of 100 µs to 1 ms.

In some embodiments and as described elsewhere herein, the first analyte 330 and the second analyte 331 are or include proteins or membrane-bound proteins. In some embodiments, one of the analytes 330 and 331 is a reference protein and the other is an unknown protein. In such case, the second detection signal 342 may be normalized to the first detection signal 340, or the first detection signal 340 may be normalized to the second detection signal 342, depending on which analyte 330 and 331 is the reference protein. In a further embodiment, one of the analytes 330 and 331 is an unmodified protein and the other is a modified or phosphorylated version of the protein. In such case, ratio of the modified or phosphorylated version of the protein to the unmodified protein may be calculated based on the measured intensities of the first detection signal 340 and the second detection signal 342.

In some embodiments and as described elsewhere herein, a plurality of samples are provided, such as in separate wells of a multi-well plate or separate blots of a membrane or other suitable substrate. Multiplexed fluorescence detection as described herein may be performed on each sample by performing, on each sample, the steps of irradiating the first fluorescent label, irradiating the second fluorescent label, measuring an intensity of the first detection signal 340, and measuring an intensity of the second detection signal 342. Each sample (typically sequentially) may be optically aligned with the first light source 310 and the first light detector 350, and with the second light source 312 and the second light detector 352. Optical alignment of the samples with selected light sources and light detectors may entail optical alignment of the samples with a cartridge removably installed in an apparatus housing of a fluorescence detection apparatus 300, such that the cartridge communicates with the fluorescence detection apparatus 300 optically and/or electrically. As described elsewhere herein, the cartridge may enclose one or more components of the fluorescence detection apparatus 300.

In other embodiments, the method may be extended to the use of three or more different fluorescent labels, and may utilize a combination of two or different classes or groups of fluorescent labels (e.g., UCPs, lanthanide chelates, transition metal chelates, etc.), which provides advantages such as significantly reduced signal channel cross-talk as described herein.

As an example of a method for triplexed fluorescence detection, the sample 332 includes a third fluorescent label bound to a third analyte 333. Antibodies and antibody conjugates, or direct binding, may be performed depending on the embodiment. The third analyte 333 may be, for example, a protein, a membrane-bound protein, a reference protein, an unknown protein, an unmodified protein, or a modified or phosphorylated version of a protein, as described herein. The third fluorescent label may be or include a non-UCP label different from the second fluorescent label. For example, the second fluorescent label may be or include a transition metal chelate, and the third fluorescent label may be or include a lanthanide chelate.

In the triplex method presently being described, the third fluorescent label is irradiated with a third excitation light 323 at a third excitation wavelength different from the first excitation wavelength and the second excitation wavelength. In response, the third fluorescent label emits a third detection signal 343 at a third emission wavelength which may be different from the first emission wavelength and the second emission wavelength. Irradiation of the third fluorescent label is then ceased, after which an intensity of the third detection signal 343 is measured at a third measurement time, which may be different from the first measurement time and the second measurement time. Measurement of the UCP-containing analyte (first analyte 330) may be acquired by normal fluorescence or TRF as described above.

In some embodiments, the first excitation wavelength is in the near-infrared range, and the first emission wavelength is in the visible range, and at least one of the second excitation wavelength and the third excitation wavelength is in the ultraviolet range. In some embodiments, the UCP of the first fluorescent label has a first fluorescence emission lifetime, the second fluorescent label has a second fluorescence emission lifetime, the third fluorescent label has a third fluorescence emission lifetime, and the first fluorescence emission lifetime is different than the second fluorescence emission lifetime and the third fluorescence emission lifetime. In some embodiments, the second fluorescence emission lifetime is longer than the third fluorescence emission lifetime by a factor of at least 5 times, or at least 50 times, or at least 100 times, or at least 500 times, or 1000 times.

EXAMPLES

Protein detection and characterization is an important task for pharmaceutical and clinical research. For example, protein detection and characterization can provide information on up and down regulation of proteins in cells, phosphorylation during cell signaling, and expression of transfected proteins. Multiple techniques have been developed for protein analysis including plate reader based enzyme-linked immunosorbent assays (ELISA), sodium dodecyl sulfate-polyacrylamide gel electrophoresis (SDS-PAGE), and spot or bead based capture systems that utilize luminescence read outs. However, improvement in analytical methods for the detection and quantitation of proteins is important to provide better tools to help understand disease mechanisms.

A number of luminescence probes have been developed to enable detection and analysis of proteins. Typically probes are attached to primary or secondary antibodies that then bind selectively to the protein of interest. These probes can be fluorescent molecules that produce light upon excitation with electromagnetic radiation or reactive species that will produce light when they are put in contact with another reactive molecule (e.g., a substrate) or some other stimulant (e.g., electrical current). Such probes are versatile as they can be attached through well-known chemical reactions to proteins, nucleotides, or small molecules. The relative amount of protein in a sample can be determined by the amount of light produced by the probes leading to the ability to do protein quantitation. Such probes also facilitate determining the spatial location of a protein of interest from low resolution (100-1000 μM) spots or blots to high resolution (<1 μM) sub-cellular imaging. These probes can be organic dyes, inorganic compounds, fluorescent proteins, or enzymes.

Chemiluminescence (CL) is a common method for detection of proteins in biochemical analyses or on surface-bound and spatially separated proteins. An example of the latter is the method of sodium dodecyl sulfate-polyacrylamide gel electrophoresis (SDS-PAGE) with electrophoretic transfer of proteins to a membrane, referred to as Western Blot (WB) analysis (Towbin et al. (1979) *Proc. Natl. Acad. Sci. U.S.A.* 76(9):4350-4354; Renart et al. (1979) *Proc. Natl. Acad. Sci. U.S.A.* 76(7):3116-3120). Electro-chemiluminescence (ECL) has also been applied to detect proteins bound to spots in specially designed multiwell plates (e.g., MULTI SPOT® and MULTI-ARRAY™ plates and SECTOR™ instruments, Meso Scale Discovery, a division of Meso Scale Diagnostics, LLC, Gaithersburg, Md.).

An advantage of CL and ECL is very high sensitivity with limits of detection for proteins in solution in the sub-picogram/ml range. However, these systems produce transient signals, are not stable, and require a complicated procedure to produce the chemical reaction required for detection. They are also non-linear systems (i.e., one probe produces many photons) and have poor reproducibility so are not suitable for applications where quantitation of protein amount is desired. A last, but significant limitation is the inability to multiplex multiple CL signals. Their emissions are very broad and that makes the ability to detect two different CL emissions from the same spatial location very challenging.

Fluorescence (FL) probes overcome some of the limitations of CL. They provide ability for better quantitation since the relationship between excitation photons and emission photons is, in general, linear. They are also more versatile as there is no need to provide access to the probes by other reactive molecules. In general, FL probes are also more stable, especially when protected from light as they are generally non-reactive chemical species. Perhaps the most important advantage of FL probes is that they provide the ability to perform multiplexing. FL molecules come in a wide variety of forms with a wide range of excitation and emission bands. Thus two (or more) probes at the same spatial location can be independently excited and detected with minimal overlap (or cross-talk) between detection channels. The ability to detect up to four independent fluorophores from the same spatial location is regularly reported using color bandpass filters. Higher levels of multiplexing have been reported with flow cytometry and multispectral imaging (Stack et al. (2014) *Methods* 70(1):46-58; Perfetto et al. (2004) 4(8):648-655).

Unfortunately, FL probes have not demonstrated the same level of sensitivity as CL and typically have a lower dynamic range. A reason for lower sensitivity with FL probes is the presence of background from autofluorescence of co-localized material or interference of fluorescence from other probes. A different technique was developed to reduce background from autofluorescence using longer lifetime fluorescent probes called time-resolved fluorescence (TRF) (Zuchner et al. (2009) *Anal. Chem.* 81(22): 9449-9453; Kemper et al. (2001) *Electrophoresis.* 22(5):881-889; Lim et al. (1997) *Anal Biochem.* 245(2):184-195; Huhtinen et al. (2005) *Anal. Chem.* 77(8):2643-2648; Vereb et al. (1998) *Biophys J.* 74(5):2210-2222). In brief, autofluorescence typically has a relatively short lifetime (<20 ns) so that TRF detection is delayed in time until after the autofluorescence signal has died away. This is technically time gated detection, but has commonly been called time resolved (Lakowicz, *"Principles of Fluorescence Spectroscopy,"* 3rd Edition, Springer-Verlag, New York, 2006). The benefits of TRF detection have been well documented and include higher sensitivity, lower background, and wider dynamic range (Eliseeva & Bunzli (2010) *Chem. Soc. Rev.* 39(1):189-227; Bunzli & Piguet (2005) *Chem. Soc. Rev.* 34(12):1048-1077; Diamandis (1991) *Clin. Chem.* 37(9):1486-1491).

Significant effort has been made to develop and optimize TRF probes based on lanthanide coordination complexes with the most popular entities based on Eu and Tb (Kemper et al. (1999) 1 Biomol. Screen. 4(6):309-314; Lopez et al. (1993) *Clin. Chem.* 39(2):196-201; Degorce et al. (2009) *Curr. Chem. Genomics.* 3:22-32). These probes have a wide range of use besides membranes and have shown good sensitivity for detection of proteins in histologic sections and in living cells (Su et al. (2005) *Anal. Biochem.* 347(1):89-93; Gahlaut & Miller (2010) *Cytometry A.* December 2010; 77(12):1113-1125). Various instruments have been developed for measurement of TRF especially for 2-dimensional arrays. The lanthanide probes can be imaged using standard camera systems with ultraviolet (UV) excitation, although reported sensitivities are only in the nanogram of protein range (Kemper et al. (2001) *Electrophoresis.* 22(5):881-889). Improvements in sensitivity can be made by using time-gated cameras with chopped or pulsed high intensity uv light sources (Gahlaut & Miller (2010) *Cytometry A.* 77(12): 1113-1125). However, this increases the overall cost of the instrumentation. A spot scanning system was developed using a pulsed uv laser and time-gated photon counting (Zuchner et al. (2009) *Anal. Chem.* 81(22):9449-9453). Excellent sensitivity for both Dot Blots and Western Blots were reported as well as extended dynamic range compared to chemiluminescence and fluorescence.

Figure 4A:
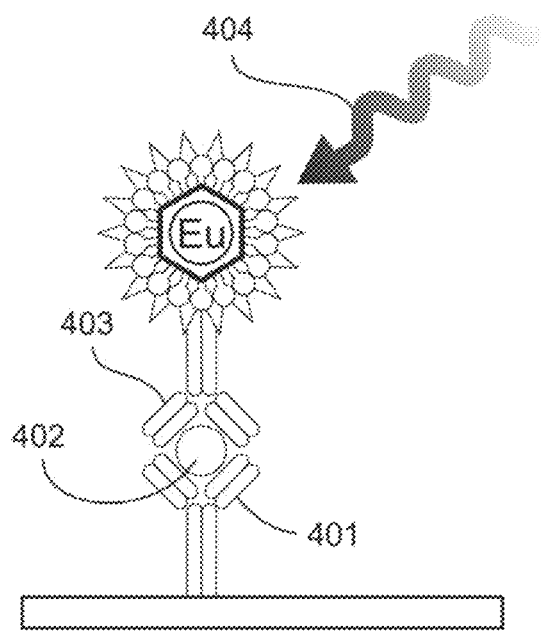
FIG. 4A is a schematic view of a method of TRF detection using a ScanLater™ Western Blot Detection System (Molecular Devices, LLC, Sunnyvale, Calif.).
Figure 4B:
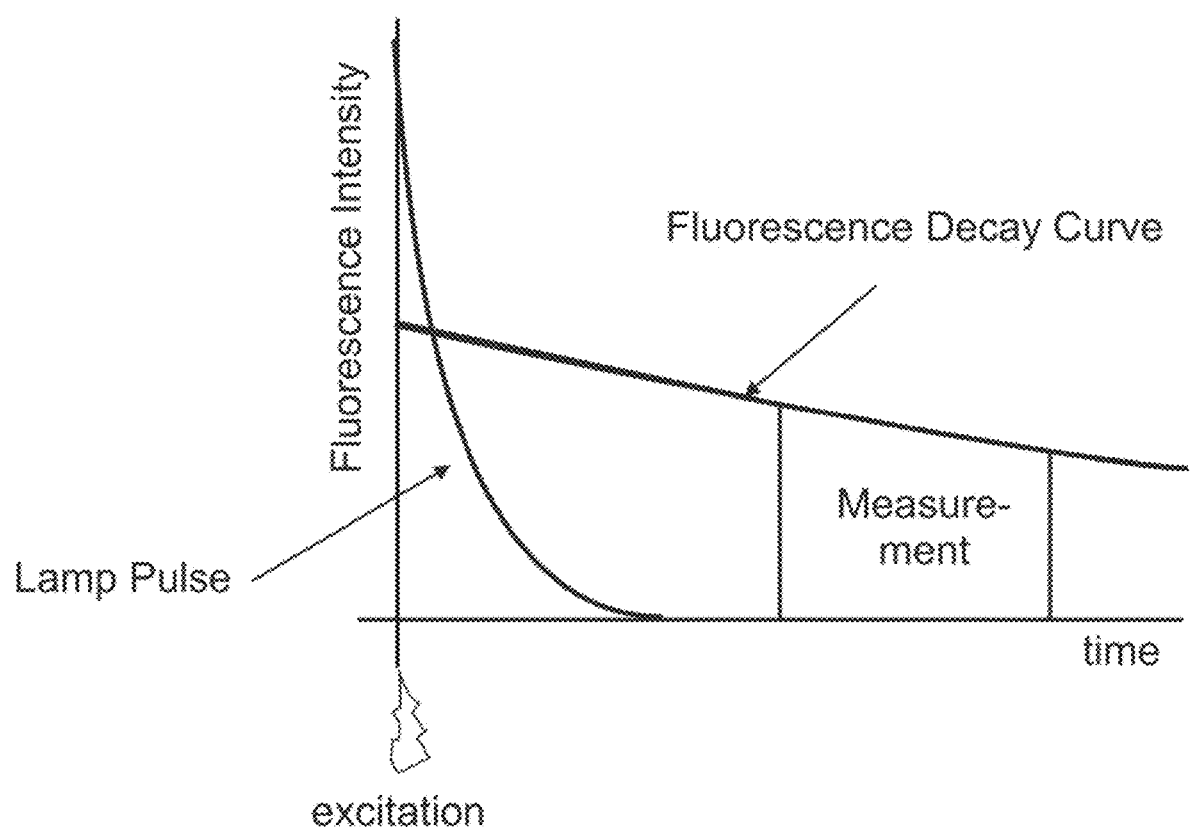
FIG. 4B is a schematic view illustrating principles of TRF detection.

We have demonstrated capability for detection and quantification of membrane bound proteins labeled with TRF stains. Membranes are incubated with Europium-chelate labeled secondary antibodies or streptavidin that bind specifically to the protein of interest. Europium (Eu) has a long fluorescence lifetime, on the order of 1 msec, and detection is done in time resolved fluorescence (TRF) mode with 50 µs delay which significantly reduces background from autofluorescence or other sources of short lifetime emissions (see FIGS. 4A and 4B). FIG. 4A is a schematic view of one non-limiting example of a method of TRF detection using the ScanLater™ Western Blot Detection System (Molecular Devices, LLC, Sunnyvale, Calif.), which in some embodiments may utilize a cartridge configured specifically for WB detection. An existing primary antibody 401 binds to a protein of interest 402. An Eu-labeled secondary antibody 403 then binds to the primary antibody 401. The ScanLater™ system is then utilized for detection (measurement) 404. It will be understood that a detection system other than the ScanLater™ system may be utilized. FIG. 4B is a schematic view illustrating principles of TRF detection. FIG. 4B plots intensity of the lamp excitation pulse and fluorescence decay as a function of time, with time=0 corresponding to the initiation of the excitation pulse. FIG. 4B also shows the period of time during which measurement may be taken relative to the preceding excitation pulse.

The membranes are placed into a plate reader system where they are scanned with a flash-lamp based TRF cartridge that has been optimized for WB scanning. The flash-lamp reduces the cost of the system as compared to the pulsed uv laser system previously reported while maintaining sensitivity (Zuchner et al. (2009), *Anal. Chem.* 81(22): 9449-9453). The method does not involve enzyme detection, and the Eu-chelates are resistant to photo-bleaching so the signal remains stable for long periods of time (weeks to months). This allows repeat reading of membranes and potential for comparison of band intensities to known standards for more accurate quantitation.

The TRF detection employs photon counting; hence the theoretical dynamic range is $>10^5$. In practice, dynamic range is limited by saturation of binding sites on high-abundance bands and non-specific binding to background membrane. There is also no camera "blooming" from saturation with high intensity light, as can occur with chemiluminescence or fluorescence detection, thus the system gives sharp bands and excellent image quality. This system provides a substrate-free environment for membrane-bound protein analysis with high sensitivity, broad dynamic range, and long-term stability. It provides advantages over current systems by allowing improved quantification and the ability to re-scan samples for reference or as instrument standards.

Figure 5A:
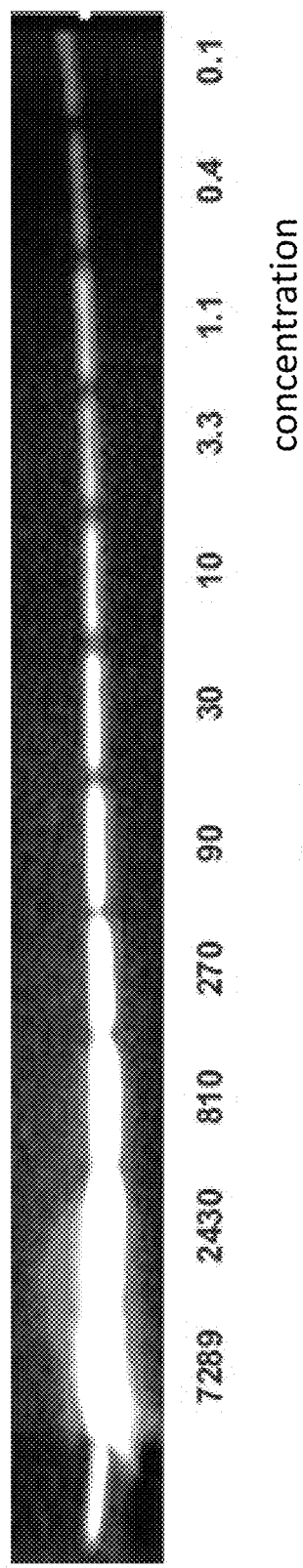
FIG. 5A is an image of a three-fold serial dilution of glutathione S-transferase (GST).
Figure 5B:
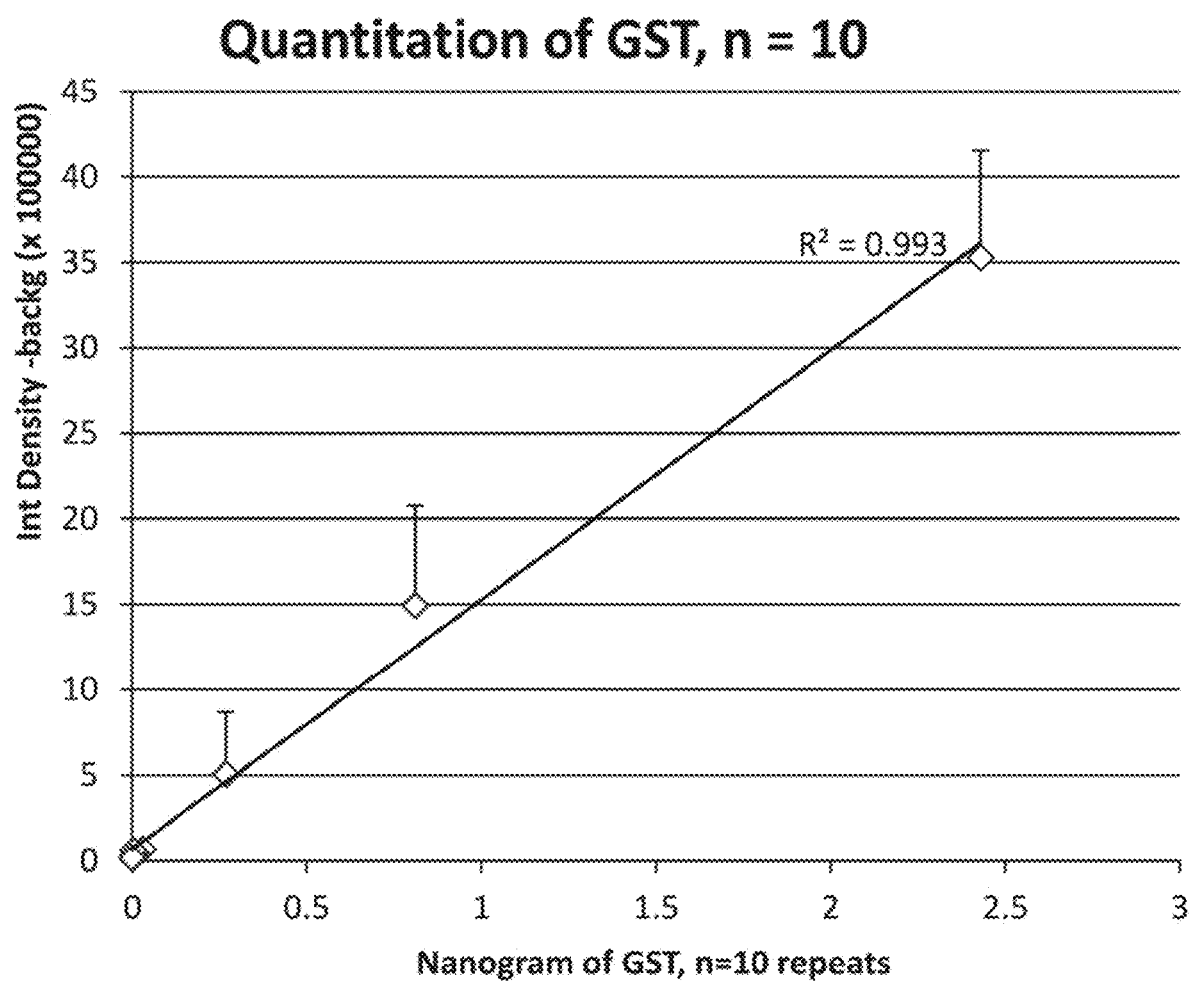
FIG. 5B is a graph of integrated intensities from individual bands across an average of 10 different Western Blots.

A three-fold serial dilution of glutathione S-transferase (GST) was used to demonstrate the dynamic range of ScanLater™ as scanned by SpectraMax® Paradigm® Multimode Detection Platform (Molecular Devices, LLC, Sunnyvale, Calif.) (see FIG. 5A). For the detection of the GST protein, biotin labeled rabbit anti-GST primary antibody was used. The ScanLater™ Eu-labeled streptavidin was used for detection. The blot was washed, dried and scanned. The system demonstrated sub-picogram detection limits of GST with over 4 logs of positive response of the signal vs. amount of GST (see FIG. 5B). FIG. 5A is an image of a GST dilution series, and FIG. 5B is a graph of integrated intensities from individual bands across an average of 10 different Western Blots.

Figure 6:
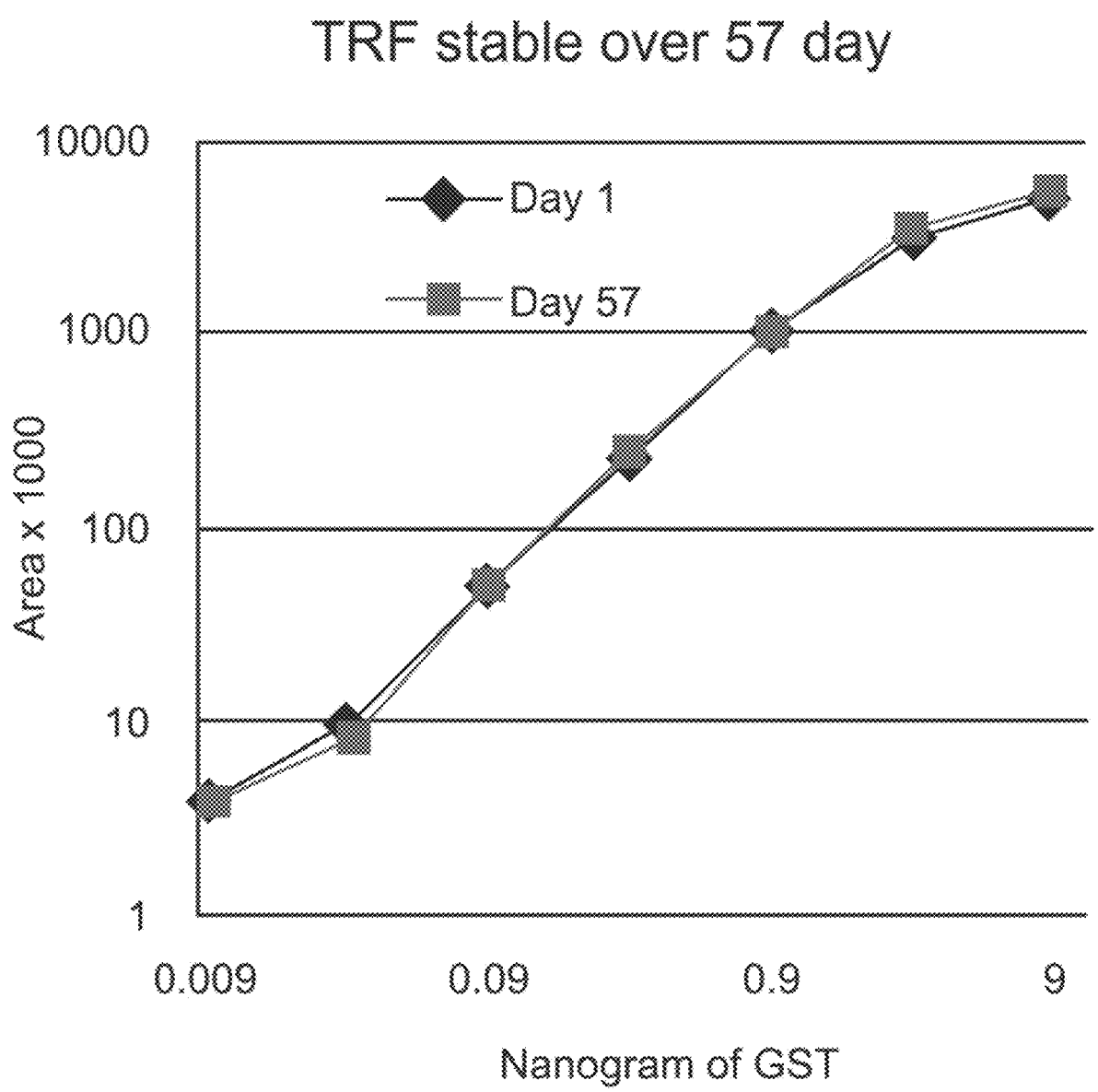
FIG. 6 is a graph showing stability of Western Blot results over time using a SpectraMax® Paradigm® reader with a ScanLater™ cartridge.

Limitations of CL and FL detection methods include signal stability. In the case of typical CL reagents, signals are stable for 5-20 minutes after which the substrate is used up and band intensity decreases. For FL, organic fluorophors are more stable when kept in appropriate conditions, but they are prone to photobleaching and signals will decay after repeated exposure to excitation light. TRF detection avoids both of these limitations and provides improved stability performance. To show long-term stability, a three-fold serial dilution of GST was used to demonstrate the signal stability over 57 days. The WB was prepared as described previously and measured immediately after preparation (Day 1) and then 57 days later after storage in a dark environment under ambient conditions. FIG. 6 is a graph showing stability of Western Blot results over time using a SpectraMax® Paradigm® reader with a ScanLater™ cartridge. The two scans were analyzed for mean band intensity over background and the results are presented in FIG. 6. No degradation of the WB or decrease in signal was observed after 57 days of storage.

Figure 7:
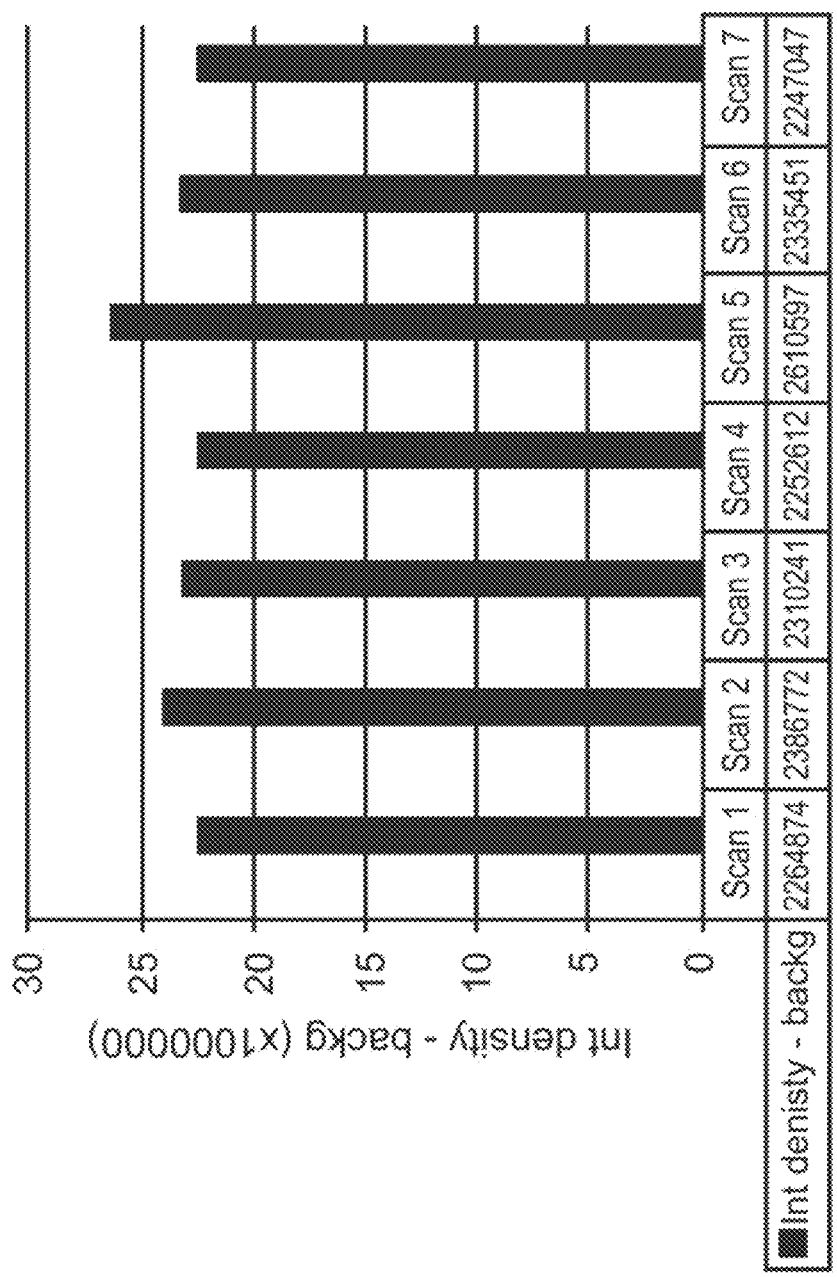
FIG. 7 is a graph showing a lack of photo-bleaching of TRF reagents after repeated scans of a single band on a Western Blot. For each scan, bars show intensity ("Int. Density").

To study the effect of photo-bleaching a WB developed with two-fold serial dilution of transferrin was subjected to repeated reads. FIG. 7 is a graph showing a lack of photobleaching of TRF reagents after repeated scans of a single band on a Western Blot. For each scan, bars showing integrated intensity ("Int. Density") are on the right. The average intensity from the 250 pg band was measured for each scan and the results are shown in FIG. 7. No systematic decrease in signal intensity was observed indicating that photo-bleaching of the TRF reagents was not an issue.

Multiplexing of TRF has been reported with some success. The use of Eu and Tb based probes has been demonstrated in biochemical assays using Time-Resolved Fluorescence Resonance Energy Transfer (TR-FRET) to detect two different proteins (Degorce et al. (2009) *Curr. Chem. Genomics.* 3:22-32; Bookout et al. (2000) 1 *Agric. Food Chem.* 48(12):5868-5873; Hamy et al. (2001) *J. Biomol. Screen.* 6(3):179-187). In addition, there have also been reports of multiplexing with Eu and Sm, and Eu, Tb, and Sm (Bador et al. (1987) *Clin. Chem.* 33(1):48-51; Heinonen et al. (1997) *Clin. Chem.* 43(7):1142-1150). The analytical schemes for these systems use a flashlamp with a single color bandpass filter for excitation and multiple emission bandpass filters.

Figure 8:
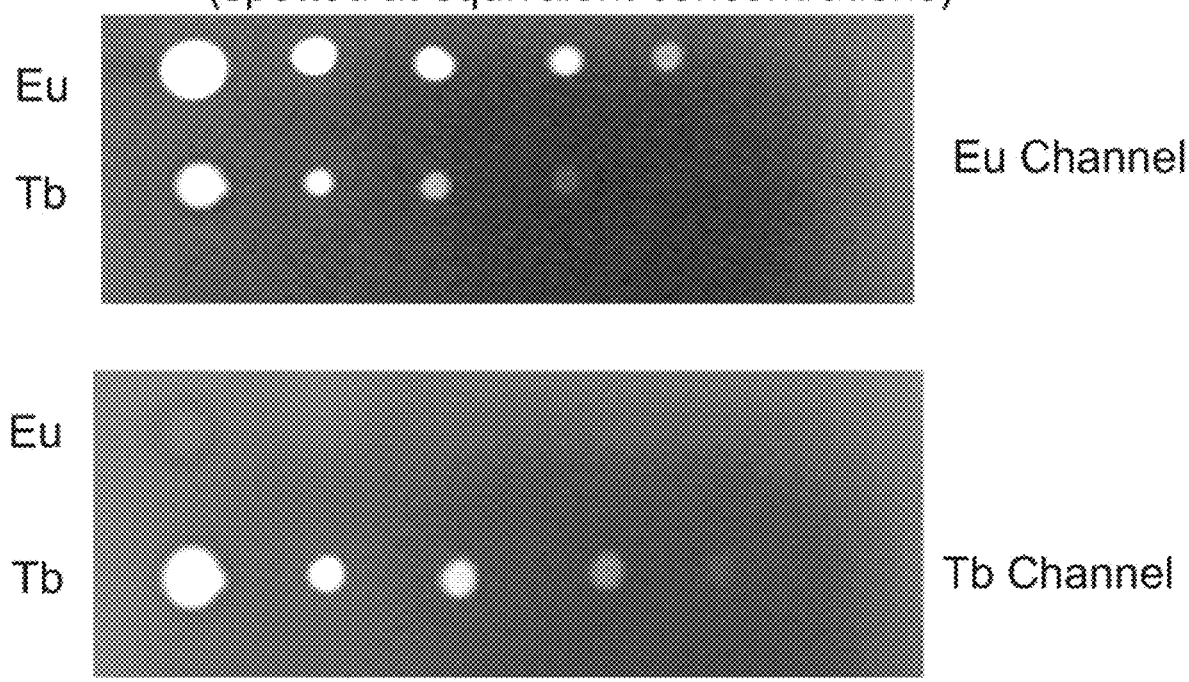
FIG. 8 shows Dot Blot results comparing cross-talk emissions between detection channels for europium (Eu) and terbium (Tb) based probes.
Figure 9:
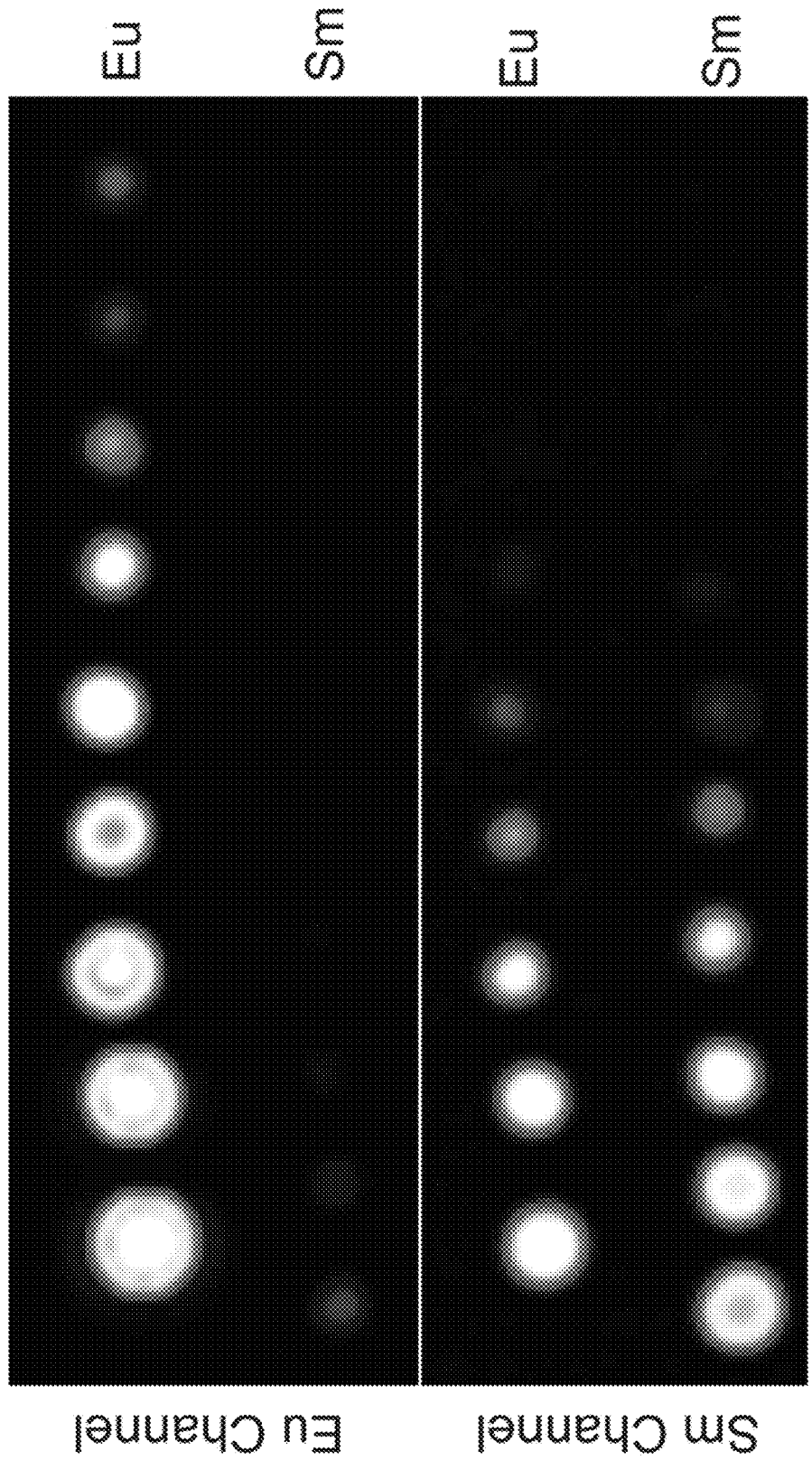
FIG. 9 shows Dot Blot results comparing cross-talk emissions between detection channels for europium (Eu) and samarium (Sm) based probes.

These systems of the prior art described above suffer from cross-talk as emission from one of the lanthanides bleeds into the detection channels of the other lanthanides. In practice, good separation can be achieved in only one of the ratios because of the abundance of emission peaks in the lanthanide spectrum. For example, with Eu and Tb there is minimal Eu signal in the Tb channel, but the Tb cross-talk into the Eu channel can be as high as 10%. Eu and Sm are reversed where there is no Sm cross-talk into the Eu channel, but significant (>10%) Eu cross-talk into the Sm channel. This limits the utility of these methods to having only one truly sensitive channel, while the other is limited by background signal from the second species. Examples of these for Eu, Tb, and Sm dot blots are shown in FIG. 8 and FIG. 9. FIG. 8 shows Dot Blot results comparing cross-talk emissions between detection channels for europium (Eu) and terbium (Tb) based probes. FIG. 9 shows Dot Blot results comparing cross-talk emissions between detection channels for europium (Eu) and samarium (Sm) based probes.

As described elsewhere herein, an aspect of the present invention concerns a novel method to multiplex long lifetime fluorescent dyes using TRF detection. We used a combination of spectral and temporal differences in fluorescence emission to enhance the ability to separate signals in an assay from multiple dyes. In some embodiments, this was reduced to practice with the combination of Ruthenium (Ru) and Europium (Eu) labels in a multiplexed Western Blot detection scheme, but also has applications to immunoassays, protein arrays, and other multiplexed biological assays. Ru has been used as a dye for detection of proteins, DNA, and other compounds and its long lifetime has been used to create analytical systems that reject shorter lifetime signals (Demas et al. (1999) *Anal. Chem.* 71(23):793A-800A; Berggren et al. (1999) *Anal. Biochem.* 276(2):129-143; Ullmer et al. (2012) *Br. J. Pharmacol.* 167(7):1448-1466). However, there have been no reports of combining Ru and Eu or other very long lifetime lanthanides in a multiplexed system.

The solution we developed exploits both time-domain and wavelength domain differences between TRF dyes to reduce cross-talk to below 1%, and more particularly to below 0.01%. Temporal Separation: Ru, whose half-life is ~1 μsec is detected with shorter time integration (2 μsec); Eu, whose half-life is ~800 μsec, is detected with longer time integration (1000 μsec). Spectral Separation: Ru is excited at 470 nm and detected at 624 nm; Eu is excited at 370 nm and detected at 616 nm.

Figure 10:
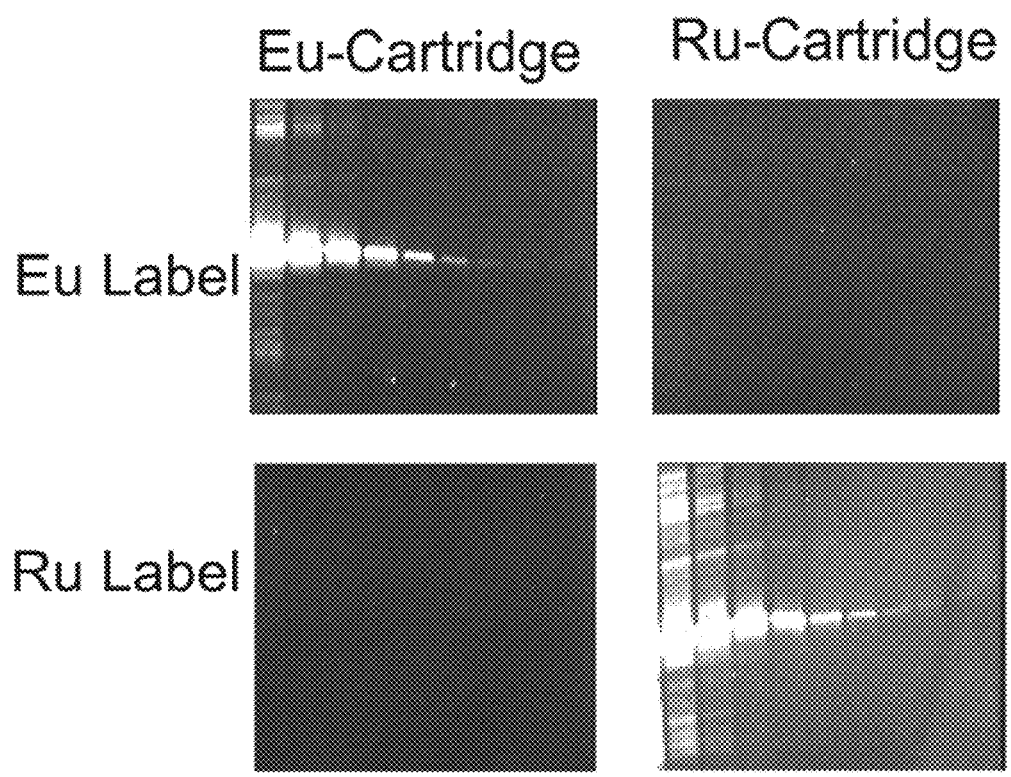
FIG. 10 shows Western Blot results of a GST dilution series comparing cross-talk emissions between detection channels with europium (Eu) and ruthenium (Ru) based probes; these scans were obtained with cartridges using laser diode excitation.

FIG. 10 shows Western Blot results of a GST dilution series comparing cross-talk emissions between detection channels with europium (Eu) and ruthenium (Ru) based probes. These scans were obtained with cartridges using laser diode excitation.

Figure 11:
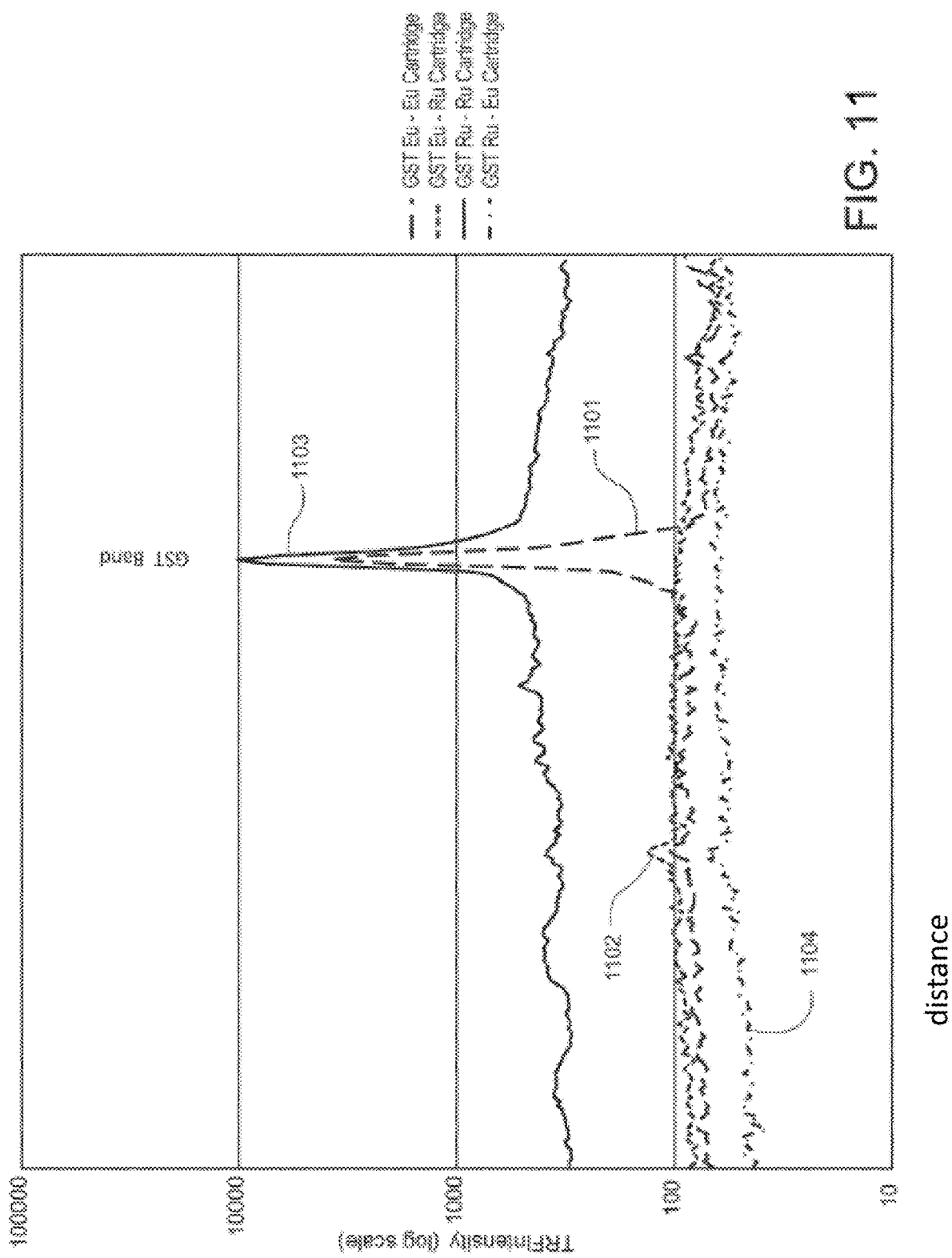
FIG. 11 is a graph showing averaged Line Scans through lanes on the Western Blots shown in FIG. 10; the line scan for the GST Eu-Eu Cartridge is labeled 1101, the line scan for the GST Eu-Ru Cartridge is labeled 1102, the line scan for the GST Ru-Ru Cartridge is labeled 1103, and the line scan for the GST Ru-Eu Cartridge is labeled 1104.

FIG. 11 is a graph showing averaged Line Scans through lanes on the Western Blots shown in FIG. 10. The line scan for the GST Eu-Eu Cartridge is labeled 1101, the line scan for the GST Eu-Ru Cartridge is labeled 1102, the line scan for the GST Ru-Ru Cartridge is labeled 1103, and the line scan for the GST Ru-Eu Cartridge is labeled 1104.

These results were obtained with two different cartridges in a SpectraMax® Paradigm® reader, but can be extended to a single cartridge that works in both SpectraMax® Paradigm® and SpectraMax® i3 Multi-Mode Microplate Reader Detection Platform systems (Molecular Devices, LLC, Sunnyvale, Calif.).

EXEMPLARY EMBODIMENTS

Exemplary embodiments provided in accordance with the presently disclosed subject matter include, but are not limited to, the following:

1. A method for multiplexed fluorescence detection, the method comprising: providing a sample comprising a first fluorescent label bound to a first analyte and a second fluorescent label bound to a second analyte, wherein the first fluorescent label comprises an upconverting phosphor (UCP) and the second fluorescent label comprises a non-UCP label; irradiating the first fluorescent label with a first excitation light at a first excitation wavelength, wherein the first fluorescent label emits a first detection signal at a first emission wavelength; irradiating the second fluorescent label with a second excitation light at a second excitation wavelength different from the first excitation wavelength, wherein the second fluorescent label emits a second detection signal at a second emission wavelength; measuring an intensity of the first detection signal at a first measurement time, wherein the intensity of the first detection signal is correlated with the amount of the first analyte in the sample; ceasing irradiating the second fluorescent label; and after ceasing irradiating the second fluorescent label, measuring an intensity of the second detection signal at a second measurement time, wherein the intensity of the second detection signal is correlated with the amount of the second analyte in the sample.

2. The method of embodiment 1, comprising measuring the intensity of the first detection signal while irradiating the first fluorescent label.

3. The method of embodiment 1, comprising ceasing irradiating the first fluorescent label and, after ceasing irradiating the first fluorescent label, measuring the intensity of the first detection signal.

4. The method of any of the preceding embodiments, wherein the sample comprises a third fluorescent label bound to a third analyte, the third fluorescent label comprises a non-UCP label different from the second fluorescent label, and the method further comprises: irradiating the third fluorescent label with a third excitation light at a third excitation wavelength different from the first excitation wavelength and the second excitation wavelength, wherein the third fluorescent label emits a third detection signal at a third emission wavelength; ceasing irradiating the third fluorescent label; and after ceasing irradiating the third fluorescent label, measuring an intensity of the third detection signal at a third measurement time.

5. The method of embodiment 4, comprising measuring the intensity of the first detection signal while irradiating the first fluorescent label.

6. The method of embodiment 4, comprising ceasing irradiating the first fluorescent label and, after ceasing irradiating the first fluorescent label, measuring the intensity of the first detection signal.

7. The method of any of embodiments 4-6, wherein the second fluorescent label comprises a transition metal chelate, and the third fluorescent label comprises a lanthanide chelate.

8. The method of any of embodiments 4-6, wherein: the second fluorescent label comprises a transition metal chelate selected from the group consisting of transition metal chelates of ruthenium (Ru(II)), osmium (Os(II)), and rhenium (Re(I)); and the third fluorescent label comprises a lanthanide chelate selected from the group consisting of lanthanide chelates of samarium (Sm(III)), dysprosium (Dy(III)), europium (Eu(III)), and terbium (Tb(III)).

9. The method of any of embodiments 4-8, wherein: the first excitation wavelength is in the near-infrared range, and the first emission wavelength is in the visible range; and at least one of the second excitation wavelength and the third excitation wavelength is in the ultraviolet range.

10. The method of any of embodiments 4-9, wherein the UCP of the first fluorescent label has a first fluorescence emission lifetime, the second fluorescent label has a second fluorescence emission lifetime, the third fluorescent label has a third fluorescence emission lifetime, and the first fluorescence emission lifetime is different than the second fluorescence emission lifetime and the third fluorescence emission lifetime.

11. The method of any of embodiments 4-9, wherein the UCP of the first fluorescent label has a first fluorescence emission lifetime, the second fluorescent label has a second fluorescence emission lifetime, the third fluorescent label has a third fluorescence emission lifetime, and the second fluorescence emission lifetime is longer than the third fluorescence emission lifetime by a factor selected from the group consisting of: at least 5 times; at least 50 times; at least 100 times; at least 500 times; and at least 1000 times.

12. The method of any of embodiments 4-9, wherein the UCP of the first fluorescent label has a first fluorescence emission lifetime, the second fluorescent label has a second fluorescence emission lifetime, and comprising at least one of: at least one of the second fluorescence emission lifetime and the third emission lifetime is in a range of 0.1 us to 10 μs; at least one of the second fluorescence emission lifetime and the third emission lifetime is in a range of 100 μs to 1 ms.

13. The method of any of embodiments 4-12, wherein at least one of the second fluorescent label and the third fluorescent label has a Stokes shift selected from the group consisting of: a Stokes shift of greater than 20 nm; a Stokes shift of greater than 100 nm; a Stokes shift of greater than 250 nm; and a Stokes shift in a range from about 250 nm to about 350 nm.

14. The method of any of embodiments 4-13, wherein the second emission wavelength is different from the first emission wavelength.

15. The method of any of embodiments 4-14, wherein the second measurement time is different from the first measurement time.

16. The method of any of embodiments 4-15, wherein the third emission wavelength is different from the first emission wavelength and the second emission wavelength.

17. The method of any of embodiments 4-16, wherein the third measurement time is different from the first measurement time and the second measurement time.

18. The method of any of the preceding embodiments, wherein providing the sample comprises: contacting the sample with: a first antibody that specifically binds the first analyte; a second antibody that specifically binds the second analyte; a third antibody that specifically binds the third analyte; a first fluorescent antibody conjugate that specifically binds the first antibody, wherein the first fluorescent antibody conjugate comprises the first fluorescent label; and a second fluorescent antibody conjugate that specifically binds the second antibody, wherein the second fluorescent antibody conjugate comprises the second fluorescent label; a third fluorescent antibody conjugate that specifically binds the third antibody, wherein the third fluorescent antibody conjugate comprises the third fluorescent label; and incubating the sample under conditions and for a time sufficient to allow the antibodies and the antibody conjugates to form immunocomplexes.

19. The method of any of embodiments 4-17, wherein providing the sample comprises contacting the sample with a first antibody that specifically binds the first analyte, a second antibody that specifically binds the second analyte, and a third antibody that specifically binds the third analyte, wherein at least one of the first fluorescent label, the second fluorescent label and the third fluorescent label is attached directly to the respective first antibody, second antibody, or third antibody.

20. The method of any of the preceding embodiments, wherein the first analyte, the second analyte, and the third analyte comprise proteins or membrane-bound proteins.

21. The method of any of the preceding embodiments, wherein at least one of the first analyte, the second analyte, and the third analyte is a reference protein, and at least one other of the first analyte, the second analyte, and the third analyte is an unknown protein, and further comprising:

normalizing the detection signal acquired from the unknown protein to the detection signal acquired from the reference protein.

22. The method of any of the preceding embodiments, wherein at least one of the first analyte, the second analyte, and the third analyte is an unmodified protein, and at least one other of the first analyte, the second analyte, and the third analyte is a modified or phosphorylated version of the protein, and further comprising calculating a ratio of the modified or phosphorylated version of the protein to the unmodified protein based on the measured intensities of the detection signals acquired from the unmodified protein and the modified or phosphorylated version of the protein.

23. The method of any of the preceding embodiments, comprising directing at least two of the first detection signal, the second detection signal, and the third detection signal through a common emission filter.

24. The method of any of the preceding embodiments, wherein the UCP comprises a lanthanide-doped or transition metal-doped inorganic compound exhibiting anti-Stokes shift.

25. The method of embodiment 24, wherein the inorganic compound comprises a dopant ion selected from the group consisting of erbium ($Er^{3+}$), thulium ($Tm^{3+}$), holmium ($Ho^{3+}$), praseodymium ($Pr^{3+}$), neodymium ($Nd^{3+}$), dysprosium ($Dy^{3+}$), ytterbium ($Yb^{3+}$), samarium ($Sm^{3+}$), and a combination of two or more of the foregoing.

26. The method of embodiment 24 or 25, wherein the inorganic compound is selected from the group consisting of a halide, an oxide, and an oxysulfide.

27. The method of any of the preceding embodiments, wherein the second fluorescent label comprises a transition metal chelate or a lanthanide chelate.

28. The method of any of the preceding embodiments, wherein the second fluorescent label comprises a transition metal chelate selected from the group consisting of transition metal chelates of ruthenium (Ru(II)), osmium (Os(II)), and rhenium (Re(I)).

29. The method of any of the preceding embodiments, wherein the second fluorescent label comprises a lanthanide chelate selected from the group consisting of lanthanide chelates of samarium (Sm(III)), dysprosium (Dy(III)), europium (Eu(III)), and terbium (Tb(III)).

30. The method of any of the preceding embodiments, wherein the first excitation wavelength is in the near-infrared range, and the first emission wavelength is in the visible range.

31. The method of any of the preceding embodiments, wherein the second excitation wavelength is in the ultraviolet range, and the second emission wavelength is longer than the second excitation wavelength.

32. The method of any of the preceding embodiments, wherein the UCP of the first fluorescent label has a first fluorescence emission lifetime, the second fluorescent label has a second fluorescence emission lifetime, and the first fluorescence emission lifetime is different than the second fluorescence emission lifetime.

33. The method of any of the preceding embodiments, wherein the UCP of the first fluorescent label has a first fluorescence emission lifetime, the second fluorescent label has a second fluorescence emission lifetime, and comprising at least one of: the second fluorescence emission lifetime is in a range of 0.1 µs to 10 µs; the second fluorescence emission lifetime is in a range of 100 µs to 1 ms.

34. The method of any of the preceding embodiments, wherein the second fluorescent label has a Stokes shift selected from the group consisting of: a Stokes shift of greater than 20 nm; a Stokes shift of greater than 100 nm; a Stokes shift of greater than 250 nm; and a Stokes shift in a range from about 250 nm to about 350 nm.

35. The method of any of the preceding embodiments, wherein the second emission wavelength is different from the first emission wavelength.

36. The method of any of the preceding embodiments, wherein the second measurement time is different from the first measurement time.

37. The method of any of the preceding embodiments, wherein providing the sample comprises: contacting the sample with: a first antibody that specifically binds the first analyte; a second antibody that specifically binds the second analyte; a first fluorescent antibody conjugate that specifically binds the first antibody, wherein the first fluorescent antibody conjugate comprises the first fluorescent label; and a second fluorescent antibody conjugate that specifically binds the second antibody, wherein the second fluorescent antibody conjugate comprises the second fluorescent label; and incubating the sample under conditions and for a time sufficient to allow the antibodies and the antibody conjugates to form immunocomplexes.

38. The method of any of embodiments 1-36, wherein providing the sample comprises contacting the sample with a first antibody that specifically binds the first analyte and a second antibody that specifically binds the second analyte, wherein the first fluorescent label is attached directly to the first antibody, or the second fluorescent label is attached directly to the second antibody, or both of the foregoing.

39. The method of any of the preceding embodiments, wherein the first analyte and the second analyte comprise proteins or membrane-bound proteins.

40. The method of any of the preceding embodiments, wherein one of the first analyte and the second analyte is a reference protein, and the other of the first analyte and the second analyte is an unknown protein, and further comprising: normalizing the second detection signal to the first detection signal, or normalizing the first detection signal to the second detection signal.

41. The method of any of the preceding embodiments, wherein one of the first analyte and the second analyte is an unmodified protein, and the other of the first analyte and the second analyte is a modified or phosphorylated version of the protein, and further comprising calculating a ratio of the modified or phosphorylated version of the protein to the unmodified protein based on the measured intensities of the first detection signal and the second detection signal.

42. The method of any of the preceding embodiments, comprising directing the first detection signal and the second detection signal through a common emission filter or through different emission filters.

43. The method of any of the preceding embodiments, wherein irradiating the first fluorescent label and irradiating the second fluorescent label are done simultaneously or sequentially.

44. The method of any of the preceding embodiments, wherein providing the sample comprises providing a plurality of samples, and further comprising: performing multiplexed fluorescence detection on each sample by performing, on each sample, the steps of irradiating the first fluorescent label, irradiating the second fluorescent label, measuring an intensity of the first detection signal, and measuring an intensity of the second detection signal.

45. The method of embodiment 44, wherein performing multiplexed fluorescence detection on each sample comprises optically aligning the respective samples with a light source configured for generating the first excitation light and the second excitation light and a light detector configured for measuring the first detection signal and the second detection signal.

46. The method of embodiment 45, wherein: optically aligning the respective samples with the light source and the light detector comprises optically aligning the respective samples with a cartridge; the cartridge is removably installed in an apparatus housing of a fluorescence detection apparatus such that the cartridge communicates with the fluorescence detection apparatus optically and/or electrically; the cartridge encloses excitation optics defining an optical path from the light source to an aligned sample, or emission optics defining an optical path from the aligned sample to the light detector, or both of the foregoing; the light source is disposed in the cartridge or in the apparatus housing; and the light detector is disposed in the cartridge or in the apparatus housing.

47. The method of any of embodiments 44-46, wherein the samples are respectively disposed in separate wells of a multi-well plate or separate blots of a membrane.

48. A fluorescence detection apparatus configured for performing at least the irradiating and measuring steps of the method of any of the preceding embodiments, the fluorescence detection apparatus comprising: a light source configured for generating the first excitation light and the second excitation light; and a light detector configured for measuring the first detection signal and the second detection signal.

49. The fluorescence detection apparatus of embodiment 48, comprising at least one of: the light source comprises a first light source configured for generating the first excitation light and a second light source configured for generating the second excitation light; the light detector comprises a first light detector configured for measuring the first detection signal and a second light detector configured for measuring the second detection signal.

50. The fluorescence detection apparatus of embodiment 49, further comprising a third light source configured for generating the third excitation light, and a third light detector configured for measuring the third detection signal.

51. A fluorescence detection apparatus, comprising: a sample support configured for supporting a sample, the sample comprising a first fluorescent label bound to a first analyte and a second fluorescent label bound to a second analyte, wherein the first fluorescent label comprises an upconverting phosphor (UCP) and the second fluorescent label comprises a non-UCP label; a light source configured for generating a first excitation light at a first excitation wavelength and a second excitation light at a second excitation wavelength different from the first excitation wavelength; a light detector configured for measuring a first detection signal emitted from the sample at a first emission wavelength in response to excitation by the first excitation light, and a second detection signal emitted from the sample at a second emission wavelength in response to excitation by the second excitation light; and a computing device configured for: controlling the light source to respectively generate the first excitation light and the second excitation light at predetermined excitation times and for predetermined durations; and controlling the light detector to measure the first detection signal at a first measurement time, and to measure the second detection signal at a second measurement time.

52. The fluorescence detection apparatus of embodiment 51, wherein the computing device is configured for receiving an electrical output from the light detector corresponding to measurements of the first detection signal and the second detection signal, and correlating the measurements with the amount of the first analyte in the sample the amount of the second analyte in the sample.

53. The fluorescence detection apparatus of embodiment 51, wherein the computing device is configured for controlling the light source to cease generating the second excitation light, and controlling the light detector to measure the second detection signal after ceasing generating the second excitation light.

54. The fluorescence detection apparatus of any of embodiments 48-53, wherein: the sample comprises a third fluorescent label bound to a third analyte, the third fluorescent label comprising a non-UCP label different from the second fluorescent label; the light source is configured for generating a third excitation light at a third excitation wavelength different from the first excitation wavelength and the second excitation wavelength; the light detector is configured for measuring a third detection signal at a third emission wavelength; and the computing device is configured for: controlling the light source to generate the third excitation light at a predetermined excitation time and for a predetermined duration; and controlling the light detector to measure the third detection signal at a third measurement time.

55. The fluorescence detection apparatus of embodiment 54, wherein the computing device is configured for controlling the light source to cease generating the third excitation light, and controlling the light detector to measure the third detection signal at a third measurement time different from the first measurement time and the second measurement time after ceasing generating the third excitation light.

56. The fluorescence detection apparatus of any of embodiments 48-55, comprising an apparatus housing, a cartridge removably installed in the apparatus housing, excitation optics configured for defining an optical path from the light source to the sample, and emission optics configured for defining an optical path from the sample to the light detector, wherein: the light source is disposed in the cartridge or in the apparatus housing; the light detector is disposed in the cartridge or in the apparatus housing; and the computing device is disposed in the apparatus housing.

57. The fluorescence detection apparatus of embodiment 56, wherein at least one of the excitation optics and the emission optics is disposed in the cartridge.

58. The fluorescence detection apparatus of any of embodiments 48-57, wherein the sample support comprises or is configured for supporting a multi-well plate or a multi-blot membrane.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 236 schematically depicted in FIG. 2. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software)

implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 236 in FIG. 2), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components. It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for multiplexed fluorescence detection, the method comprising:
    providing a sample comprising a first fluorescent label bound to a first analyte and a second fluorescent label bound to a second analyte, wherein the first fluorescent label comprises an upconverting phosphor (UCP) and the second fluorescent label comprises a non-UCP label;
    irradiating the first fluorescent label with a first excitation light at a first excitation wavelength, wherein the first fluorescent label emits a first detection signal at a first emission wavelength;
    irradiating the second fluorescent label with a second excitation light at a second excitation wavelength different from the first excitation wavelength, wherein the second fluorescent label emits a second detection signal at a second emission wavelength;
    measuring an intensity of the first detection signal at a first measurement time, wherein the intensity of the first detection signal is correlated with the amount of the first analyte in the sample;
    ceasing irradiating the second fluorescent label; and
    after ceasing irradiating the second fluorescent label, measuring an intensity of the second detection signal at a second measurement time, wherein the intensity of the second detection signal is correlated with the amount of the second analyte in the sample,
    wherein the sample comprises a third fluorescent label bound to a third analyte, the third fluorescent label comprises a non-UCP label different from the second fluorescent label, and the method further comprises:
    irradiating the third fluorescent label with a third excitation light at a third excitation wavelength different from the first excitation wavelength and the second excitation wavelength, wherein the third fluorescent label emits a third detection signal at a third emission wavelength;
    ceasing irradiating the third fluorescent label; and
    after ceasing irradiating the third fluorescent label, measuring an intensity of the third detection signal at a third measurement time.

2. The method of claim 1, comprising measuring the intensity of the first detection signal while irradiating the first fluorescent label.

3. The method of claim 1, comprising ceasing irradiating the first fluorescent label and, after ceasing irradiating the first fluorescent label, measuring the intensity of the first detection signal.

4. The method of claim 1, wherein: the second fluorescent label is selected from the group consisting of: a transition metal chelate, a transition metal chelate of ruthenium (Ru (II)), a transition metal chelate of osmium (Os(II)), and a transition metal chelate of rhenium (Re(I)); and the third fluorescent label is selected from the group consisting of: a lanthanide chelate, a lanthanide chelate of samarium (Sm (III)), a lanthanide chelate of dysprosium (Dy(III)), a lanthanide chelate of europium (Eu(III)), and a lanthanide chelate of terbium (Tb(III)).

5. The method of claim 1, comprising at least one of:
wherein the third emission wavelength is different from the first emission wavelength and the second emission wavelength;
wherein the third measurement time is different from the first measurement time and the second measurement time.

6. The method of claim 1, wherein the UCP comprises at least one of:
a lanthanide-doped or transition metal-doped inorganic compound exhibiting anti-Stokes shift; a lanthanide-doped or transition metal-doped inorganic compound, wherein the inorganic compound comprises a dopant ion selected from the group consisting of erbium ($Er^{3+}$), thulium ($Tm^{3+}$), holmium ($Ho^{3+}$), praseodymium ($Pr^{3+}$), neodymium ($Nd^{3+}$), dysprosium ($Dy^{3+}$), ytterbium ($Yb^{3+}$), samarium ($Sm^{3+}$), and a combination of two or more of the foregoing;
a lanthanide-doped or transition metal-doped inorganic compound, wherein the inorganic compound is selected from the group consisting of a halide, an oxide, and an oxysulfide.

7. The method of claim 1, wherein the second fluorescent label is selected from the group consisting of: a transition metal chelate; a transition metal chelate of ruthenium (Ru (II)); a transition metal chelate of osmium (Os(II)); a transition metal chelate of rhenium (Re(I)); a lanthanide chelate; a lanthanide chelate of samarium (Sm(III)); a lanthanide chelate of dysprosium (Dy(III)); a lanthanide chelate of europium (Eu(III)); and a lanthanide chelate of terbium (Tb(III)).

8. The method of claim 1, wherein the first excitation wavelength is in the near-infrared range, and the first emission wavelength is in the visible range.

9. The method of claim 1, wherein the second excitation wavelength is in the ultraviolet range, and the second emission wavelength is longer than the second excitation wavelength.

10. The method of claim 1, wherein the UCP of the first fluorescent label has a first fluorescence emission lifetime, the second fluorescent label has a second fluorescence emission lifetime, and the first fluorescence emission lifetime is different than the second fluorescence emission lifetime.

11. The method of claim 1, wherein the UCP of the first fluorescent label has a first fluorescence emission lifetime, the second fluorescent label has a second fluorescence emission lifetime, and comprising at least one of: the second fluorescence emission lifetime is in a range of 0.1 µs to 10 µs; the second fluorescence emission lifetime is in a range of 100 µs to 1 ms.

12. The method of claim 1, wherein the second fluorescent label has a Stokes shift in a range from 250 nm to 350 nm.

13. The method of claim 1, comprising at least one of: wherein the second emission wavelength is different from the first emission wavelength; wherein the second measurement time is different from the first measurement time.

14. The method of claim 1, wherein providing the sample comprises: contacting the sample with: a first antibody that specifically binds the first analyte; a second antibody that specifically binds the second analyte; a first fluorescent antibody conjugate that specifically binds the first antibody, wherein the first fluorescent antibody conjugate comprises the first fluorescent label; and a second fluorescent antibody conjugate that specifically binds the second antibody, wherein the second fluorescent antibody conjugate comprises the second fluorescent label; and incubating the sample under conditions and for a time sufficient to allow the antibodies and the antibody conjugates to form immunocomplexes.

15. The method of claim 1, wherein providing the sample comprises contacting the sample with a first antibody that specifically binds the first analyte and a second antibody that specifically binds the second analyte, wherein the first fluorescent label is attached directly to the first antibody, or the second fluorescent label is attached directly to the second antibody, or both of the foregoing.

16. The method of claim 1, wherein the first analyte and the second analyte comprise proteins or membrane-bound proteins.

17. The method of claim 1, wherein one of the first analyte and the second analyte is a reference protein, and the other of the first analyte and the second analyte is an unknown protein, and further comprising: normalizing the second detection signal to the first detection signal, or normalizing the first detection signal to the second detection signal.

18. The method of claim 1, wherein one of the first analyte and the second analyte is an unmodified protein, and the other of the first analyte and the second analyte is a modified or phosphorylated version of the protein, and further comprising calculating a ratio of the modified or phosphorylated version of the protein to the unmodified protein based on the measured intensities of the first detection signal and the second detection signal.

19. The method of claim 1, comprising directing the first detection signal and the second detection signal through a common emission filter or through different emission filters.

20. The method of claim 1, wherein irradiating the first fluorescent label and irradiating the second fluorescent label are done simultaneously or sequentially.

21. The method of claim 1, wherein providing the sample comprises providing a plurality of samples, and further comprising: performing multiplexed fluorescence detection on each sample by performing, on each sample, the steps of irradiating the first fluorescent label, irradiating the second fluorescent label, measuring an intensity of the first detection signal, and measuring an intensity of the second detection signal.

22. The method of claim 21, wherein performing multiplexed fluorescence detection on each sample comprises optically aligning the respective samples with a light source configured for generating the first excitation light and the second excitation light and a light detector configured for measuring the first detection signal and the second detection signal.

23. The method of claim 22, wherein:
optically aligning the respective samples with the light source and the light detector comprises optically aligning the respective samples with a cartridge;
the cartridge is removably installed in an apparatus housing of a fluorescence detection apparatus such that the cartridge communicates with the fluorescence detection apparatus optically and/or electrically;
the cartridge encloses excitation optics defining an optical path from the light source to an aligned sample, or emission optics defining an optical path from the aligned sample to the light detector, or both of the foregoing;
the light source is disposed in the cartridge or in the apparatus housing; and the light detector is disposed in the cartridge or in the apparatus housing.

* * * * *